United States Patent
Allen

(12) 
(10) Patent No.: US 6,361,806 B1
(45) Date of Patent: Mar. 26, 2002

(54) COMPOSITION FOR AND METHOD OF TOPICAL ADMINISTRATION TO EFFECT CHANGES IN SUBCUTANEOUS ADIPOSE TISSUE

(76) Inventor: Michael P. Allen, 4900 Cedar La., Pell City, AL (US) 35128

( * ) Notice: Subject to any disclaimer, the term of this patent is extended or adjusted under 35 U.S.C. 154(b) by 0 days.

(21) Appl. No.: 09/511,056

(22) Filed: Feb. 23, 2000

(51) Int. Cl.$^7$ .................. A61K 35/78; A01N 65/00
(52) U.S. Cl. ............... 424/740; 424/725; 424/764; 424/776; 424/401; 424/486; 424/484; 514/886; 514/887; 514/899
(58) Field of Search ............... 424/401, 70.1, 424/70.11, 70.16, 70.31, 175.1, 740, 725, 764, 486, 484, 776; 514/886, 887, 899

(56) References Cited

U.S. PATENT DOCUMENTS 5,811,129 A * 9/1998 Friedman et al. ........... 424/535
5,945,409 A * 8/1999 Crandall ................. 514/78
5,989,536 A * 11/1999 Deckner et al. ......... 424/78.05

* cited by examiner

Primary Examiner—Thurman K. Page
Assistant Examiner—Liliana Di Nola-Baron
(74) Attorney, Agent, or Firm—John S. Sundsmo

(57) ABSTRACT

Emollient compositions for topical administration consisting of hydrophilic:hydrophobic emulsions containing a polyacrylate carrier, a vehicle, a mixture of $C_{16:0}$, $C_{18:0}$, $C_{18:1}$ fatty acids and derivatives as penetrants, a balanced mixture of unsaturated $C_{18:2}$, $C_{18:2}$ and $C_{18:3}$ fatty acids, a natural anti-inflammatory compound, a natural analgesic compound, a natural estrogenic compound and a fragrance; Methods of their use for ameliorating symptoms of disease including mammary fibrocystic disease, cyclic mastitis, inflammation and general and specific pre- and post-menopausal pain and swelling.

35 Claims, No Drawings

COMPOSITION FOR AND METHOD OF TOPICAL ADMINISTRATION TO EFFECT CHANGES IN SUBCUTANEOUS ADIPOSE TISSUE

FIELD OF THE INVENTION

The invention relates generally to compositions and methods for treating conditions by topical administration of agents effecting changes in subcutaneous adipose tissue, and specifically to compositions and methods for ameliorating symptoms of disease and treating physical cosmetic conditions.

BACKGROUND OF THE INVENTION

Demographics of population aging has focused special attention on pre- and post-menopausal diseases and breast cancer. About 60% of women reportedly develop palpable cysts by age 40 to 50. While retrospective studies have suggested possible relationships between fibrocystic breast disease, benign breast pain, cyclic mastalgia, benign cysts and increased risk of breast cancer, unfortunately, obvious treatment options have not been forthcoming. In younger women, fibrocystic disease is a common under-diagnosed problem with reported prevalence ranging in different studies from 41% to 69% (1–3; Citations follow the EXAMPLES section, below). It is not clear at present whether microcysts are a normal part of the breast involution process (4) and no specific United States standards of treatment exist (at present) for these conditions. With an unknown etiology, hormone therapy (5,6), caffeine restriction (7) and diet (8–11) have all been suggested as possible treatment options.

In other tissues, age related changes have also been observed. Histologic changes in cutaneous tissues accompanying aging have been evaluated at a cellular level in vitro, with a variety of findings. For example, changes have been observed in extracellular matrix components, (e.g., breakdown and UV damage to collagen fibers and elastin filaments), capillary endothelium (e.g., telangiectasia), loss of elasticity in smooth muscle fibers and changes in cholesterol, triglyceride and fatty acid metabolism.

Unlike plants, animal tissues have a limited ability to desaturate fatty acids, necessitating the intake of essential unsaturated fatty acids. Metabolism of essential fatty acids produces eicosanoids ($C_{20}$ fatty acids) including the inflammatory mediators known as prostaglandins, thromboxanes and leukotrienes. On a cellular level, membrane composition and content of unsaturated fatty acids are thought to influence membrane fluidity. Physiologically, high plasma ratios of poly-unsaturated fatty acids to saturated have been associated with lowering of cholesterol and lowering of risk of coronary heart disease and stroke. Dietary control of eicosanoid synthesis has been suggested as a means of disease intervention. Unfortunately, fatty acid metabolism is affected by variable dietary absorption rates, levels of certain hormones, (e.g, insulin, glucagon and steroid hormones), lipoproteins, triglycerides and chylomicrons, as well as tissue stores of fatty acids. These multiple factors make stable dietary control difficult to achieve. Many biologically important fatty acid mediators are also highly labile and not easily administered. Under physiologic conditions, such mediators are generated locally within tissues where they normally act to produce their effects.

Linoleic acid ($C_{18:2}$) is an essential fatty acid having two double bonds, i.e., $C_9=C_{10}$ and $C_{12}=C_{13}$ (as carbon atoms are numbered from the carboxyl terminus of the fatty acid). α-Linolenic acid ($C_{18:3}$) is an essential fatty acid having three double bonds, i.e., $C_9=C_{10}$, $C_{12}=C_{13}$ and $C_{14}=C_{15}$ as numbered from the carboxyl terminal. Linoleic, α-linolenic and arachidonic acids are the only fatty acids known to be nutritionally essential. In many animal species linoleic acid can be converted in endoplasmic reticulum (microsomes) through γ-linolenic acid ($C_6=C_7$, $C_9=C_{10}$, $C_{12}=C_{13}$; GLA) and dihomo-γ-linolenic acid ($C_8=C_9$, $C_{11}=C_{12}$, $C_{14}=C_{15}$) into arachidonic acid (i.e., $C_{20:4}$; $C_5=C_6$, $C_8=C_9$, $C_{11}=C_{12}$, $C_{14}=C_{15}$). Because of the energy dependent requirements (i.e., for NADH and NADPH), the latter process is sensitive to fasting, e.g., extreme dieting, but also malnutrition such as may occur as a result of intravenous feeding, kidney dialysis, liver cirrhosis, endotoxemia and cachesia and chemotherapy in cancer patients. Radiation therapy can also induce membranous fatty necrosis in breast tissues with resultant recurrent lumps (15).

Maternal milk contains linoleic acid and infant formula milks commonly contain essential fatty acids, including linoleic, to prevent cerebral cortical deficiency. Patients with nutritional deficiency in essential fatty acids manifest symptoms of scaly skin that is responsive to oral feeding of linoleate. Linolenic acid and evening primrose oil (rich in gamma-linolenic acid) have been evaluated for possible beneficial skin effects in hemodialysis patients with skin symptoms (13). Levels of linoleic acid can influence insulin responsiveness of vascular smooth muscle cells, and feeding a diet high in linoleic acid to Dahl sensitive hypertensive rats reportedly potentiated hypertension (12).

Nutritionally derived plasma fatty acids are known to control the rate of hepatic lipogenesis in mammals. Lipogenesis involves conversion of glucose, pyruvate and lactate to acyl-CoA intermediates and, after undergoing sequential chain elongation reactions in the endoplasmic reticulum, fatty acids are formed. Carbohydrate, glucose and insulin levels all influence fatty acid metabolism, but conversely, recent studies in rats have suggested that dietary omega-3 fatty acids (i.e., α-linolenic acid) can influence insulin binding and insulin-stimulated glucose transport and lipogenesis in muscle and adipocytes (14).

Arachidonic acid metabolites have a variety of hormone-like effects in tissues and also mediate important protective inflammatory activities: i.e., certain thromboxanes have vasoconstrictor and platelet activating activity; certain prostacyclins are vasodilators; Prostaglandin E2 enhances vascular permeability, is pyrogenic, enhances pain, and can exert immunosuppressive effects on mast cells (involved in allergy) and lymphocytes and macrophages (involved in immune defense). Dietary linoleic acid, but not gamma-linolenic acid reportedly improved aggregation responses of platelets collected from patients with liver cirrhosis (16). Novel diets low in linoleic acid and containing eicosapentaenoic acid (EPA) and gamma-linolenic acid have been considered for enteral use to reduce endotoxemia (17).

Adipocytes are a major site of fatty acid metabolism, lipogenesis, and production of lipid mediators that exert effects on surrounding tissues. Adipocytes store fatty acids in special intracellular fat vacuoles. Adipocytes are also reported to provide a stored source of estrogen in breast tissues with levels of intracellular estrogen changing during the menstral cycle and in menopause (18). Certain studies suggest a major role for adipose tissue in post-menopausal aromatase P450 catalyzed conversion of $C_{19}$ steroids to estrogens (19) and in breast tissues of women with breast cancer (20, 21). Stromal-epithelial cell interactions in breast cancer are recently reviewed (22). Growth rates of estrogen receptor positive mammary adenocarcinomas are increased in the presence of estrogens. Treatments altering endogenous estrogen synthesis in breast tissues would be highly desirable.

Effects of conjugated linoleic acid (CLA), but not linoleic acid, include inhibition of proliferation and induction of apoptosis in primary rat mammary epithelial cultures (23). In 3T3-L1 cultures of preadipocytes, CLA reportedly inhibits proliferation but stimulates differentiation, i.e., as judged by cellular lipid filling (24,25). Correlations have recently been reported between concentration of fatty acids in adipose tissue in breast cancer patients and adipocyte size in breast tissues (26). Dietary supplementation of lactating Holstein cows with 2.2% safflower oil (containing linoleic and linolenic acid) reportedly increased milk production and quantities of $C_{18:0}$, $C_{18:1}$ and $C_{18:2}$ fatty acids in milk (27). Unfortunately, dietary CLA has been associated with increased fatty streak formation in a mouse atherosclerosis model (28); altered ketogenesis and lipid secretion by rat liver (29); and undesirable effects on platelets (30).

Effects of dietary GLA include preventing sciatic nerve conduction velocity deficits in neonatal diabetic rats (31, 32) and humans (33), but suppressing immune responsiveness of lymphocytes as measured by mitogen-induced proliferation (34). GLA is reportedly cytotoxic in vitro for certain cancer cells (35,36), presumably by promoting cytotoxic lipid peroxidative mechanisms and/or upregulating expression of tumor suppressor genes (37). GLA also inhibits tumor cell motility (38), i.e., perhaps by up-regulating expression of catenins and increasing cell adhesion (39). GLA (but not linoleic acid) may also influence strength of tight junctions between endothelial cells inhibiting tumor metastasis (40). In vivo, dietary GLA reportedly altered growth and metastasis of mammary tumors (41) in mice and decrease incidence of benzanthracene-induced tumors in rats (42). In contrast, dietary LA reportedly promoted growth and metastasis of human prostatic cancer lines in SCID mice (43), CLA was inhibitory in this tumor-host system (44), but CLA was without effect in studies of human mammary tumor lines (45). Similar confounding results have been reported from in vitro studies with cyclooxygenase and lipogenase inhibitors and human mammary epithelial and MCF-7 breast carcinoma cells (46).

PPAR-alpha (PPARα) and PPAR-delta (PPARδ; pereoxisome proliferator-activated receptor) bind and are activated by linolenic acid and carbaprostacyclin in sebaceous epithelial cell cultures and linolenic acid reportedly drives sebocyte maturation (47). PPAR-gamma (PPARγ), but not PPARα or PPARδ, reportedly regulates differentiation of adipocytes (48), plays a role in sebocyte maturation (47) and drives terminal differentiation in breast adenocarcinoma cell lines (49). Mutations in PPARγ have been identified in breast cancer and colon cancer (50) cells. In tissue culture, preadipocytes reportedly stimulate growth of mammary carcinoma cell lines while mature adipocytes expressed inhibitory activity (51). Interestingly, the latter effects of adipocytes and preadipocytes seemed more pronounced in estrogen responsive cell lines than in estrogen non-responsive cell lines.

A variety of fatty acid triglyceride esters have been used relatively indiscriminantly as emollients in topical creams, oils and gels with a variety of different possible penetrant properties. For example, SaNogueira et al. (U.S. patent Ser. No. 6,001,377; Procter & Gamble; issued Dec. 14, 1999) disclose compositions containing certain triglyceride esters, acetoglyceride esters, ethoxylated glycerides, alkyl esters of fatty acids, alkenyl esters of fatty acids, fatty alcohols, polyhydric alcohol esters, wax esters, vegetable waxes, phospholipids, sterols and fatty acid amides, i.e., all as possible skin conditioning compounds in group with polyhydric alcohols, guanidine, glycolic acids and their salts, and propoxylated glycerols.

The pharmacologic arts are notoriously unpredictable, necessitating clinical and animal trials to determine therapeutically efficacy, metabolism and toxicity. Tissue penetrant topical compositions constitute a highly desirable class of pharmacologic agents. Objects of the invention provide compositions capable of regulating adipocyte metabolism in general, and fatty acid metabolism in particular, in subcutaneous adipose tissue. In other objects, the invention provides treatments for ameliorating symptoms of mammary fibrocystic disease, cyclic mastitis, inflammation and general and specific pre- and post-menopausal pain and swelling.

SUMMARY OF THE INVENTION

Emollient compositions and methods are disclosed that allow topical administration of a balanced mixture of $C_{18}$ unsaturated fatty acids that is effective to penetrates epithelial barriers and stimulate changes in fatty acid metabolism in subcutaneous adipose tissues. The compositions consist of hydrophilic:hydrophobic emulsions containing a polyacrylate carrier, a vehicle, a compatible balanced fatty acid penetrant consisting of $C_{16:0}$, $C_{18:0}$, $C_{18:1}$ fatty acid derivatives, a mixture of medicinal unsaturated $C_{18:2}$, $C_{18:2}$ and $C_{18:3}$ fatty acids, a natural anti-inflammatory compound, a natural analgesic compound, a natural estrogenic compound and a fragrance. Methods are disclosed for ameliorating symptoms of disease including mammary fibrocystic disease, cyclic mastitis, inflammation and general and specific pre- and post-menopausal pain and swelling.

DETAILED DESCRIPTION OF THE PREFERRED EMBODIMENT

It has been discovered that certain topically applied $C_{18}$ fatty acids are capable of altering metabolism in subcutaneous adipose tissues when applied topically in an emollient delivery vehicle which is capable of penetrating the epidermis and reaching subcutaneous adipose tissues. While not wishing to be tied to any particular mechanisms of action, it is believed highly likely that topically applied $C_{18}$ fatty acids penetrate the skin, and without entering capillary circulation, are passaged through the tissue, perhaps cell-to-cell (e.g., through junctional complexes), resulting in a highly specific and highly desirable distribution into local subcutaneous adipose tissues without systemic spread, dilution or side-effect. The topical compositions disclosed herein achieve the requisite rate and concentration of delivery into subcutaneous adipose tissues to produce effects in tissue metabolism with resultant amelioration of disease. The compositions have also been found useful for ameliorating physical cosmetic defects. Results suggest that the resultant tissue distribution of the instant compositions is effective to: (i) promote lipogenesis (resulting in increased adipocyte lipid vesicles and cell volume); (ii) alter synthesis of inflammatory mediators (reducing inflammation and endothelial vascular permeability); and (iii) promote local tissue synthesis of estrogen and other steroid hormones, i.e. decreasing inflammation, pain and adverse effects of the menstrual cycle and menopause. It is believed highly likely that the $C_{18}$ fatty acids applied according to the invention are inter-converted in adipose tissues by delta-6-desaturase into higher fatty acid metabolites, e.g., GLA. This result is apparently achieved without adverse effecting general tissue fatty acid metabolism, i.e., through the rate limiting stearoyl CoA desaturase, and these results are unexpected for the following reasons: namely, 1. Interconversion of linoleic acid ($C_{18:2}$) to alpha-linolenic ($C_{18:3}$), gamma-linolenic ($C_{18:3}$) and higher unsaturated fatty acids (e.g., $C_{20:4}$ arachidonic acid) involves relatively unpredictable regulatory effects on delta-6-desaturase: e.g., possible up-regulation of delta-6-desaturase by linoleic acid but down-regulation by conjugated linoleic acid;
2. The activity of the delta-6-desaturase enzyme is reportedly decreased in vitamin B6 deficiency and aging, but increased in fatty acid deficiency diseases, i.e., patient physiology apparently dictating the outcome;
3. GLA reportedly decreases delta-6-desaturase enzymatic conversion of alpha-linolenic acid (but not linoleic acid) to higher metabolites, and docosahexaenoic acid or eicosapentaenoic acid similarly decreased conversion of linoleic acid to higher metabolites, i.e., ongoing fatty acid metabolism in a diseased tissue being determinative of the effect achieved; and,
4. Transcriptional up-regulation of the stearoyl CoA desaturase gene reportedly is induced by hormones such as insulin and dexamethasone and metabolites such as glucose, with down-regulation in the presence of polyunsaturated fatty acids, (acting at different response elements in the gene), i.e., tissue metabolism at the time of administration perhaps determining the types of treatment side-effects on general fatty acid metabolism.

Unexpectedly, a topical balanced mixture of $C_{18:1}$, $C_{18:2}$ and $C_{18:3}$ fatty acids was discovered which is believed to act upon adipose tissue by decreasing endogenous stearoyl CoA desaturase activity while at the same time promoting delta-6-saturase conversion of linoleic acid ($C_{18:2}$) and alpha-linolenic acid ($C_{18:3}$) into higher metabolites such as GLA ($C_{18:3}$) and arachidonic acid ($C_{20:4}$). Low levels of GLA in the compositions likely stimulates instead of inhibiting delta-6-desaturase activity, i.e., perhaps by up-regulating expression. Induced tissue fatty acid metabolism and delta-6-desaturase likely confer the observed longer lasting effects of the instant compositions. Topical administration of the instant compositions is believed to reduce total tissue saturated fatty acids and increase unsaturated fatty acids, e.g. in adipocyte, endothelial and epithelial cell membrane phospholipids. The induced changes in saturation of tissue $C_{18}$ fatty acids are believed advantageous for at least the following reasons: namely, 1. Peroxisome activating receptors gamma (PPARγ) are likely regulated by cellular content of $C_{18:2}$ unsaturated fatty acids, i.e., PPARγ is a ligand binding steroid hormone super-family of nuclear transcription regulatory factors that is up-regulated in breast cancer. Down-regulation of PPARγ by cellular $C_{18}$ fatty acids may drive terminal differentiation in pre-malignant and malignant cells;
2. Over-expression of stearoyl CoA desaturase has been observed in carcinogen-induced mammary carcinomas and the increase may relate to altered PPARγ activity. Returning stearoyl CoA desaturase activity to more normal levels is likely to have an advantageous effect, perhaps decreasing tumor growth rate;
3. The degree of saturation of membrane phospholipids is important in determining cellular responsiveness to growth factors (e.g., protein kinase signalling) and apoptotic signalling (e.g., induced by Fas ligand). It is believed likely that changing saturation of cell membrane $C_{18}$ fatty acids is helpful in restoring a more normal pattern of responsiveness of tumor cells to growth control and in limiting metastasis;
4. Changes in preadipocyte $C_{18}$ fatty acid metabolism, possibly relating to PPARγ expression, have been implicated in processes of differentiation of preadipocytes into adipocytes. It is believed likely that driving terminal differentiation in adipose tissues will decrease incidence of cysts, lipomas and the like;
5. Observed tissue effects of TNF-α on fatty acid metabolism, e.g., in tumor cachexia, may also be mediated through PPARγ and $C_{18}$ fatty acid metabolism. It is believed likely that increasing cellular levels of unsaturated $C_{18}$ PPARγ-fatty acid ligands will result in advantageous down-regulation of PPARγ effects on cellular fatty acid metabolism in cachexia, malnutrition, endotoxemia and the like;
6. It is believed likely that increasing levels of unsaturated $C_{18}$ fatty acids in connective tissues surrounding blood vessels will result in production of desirable eicosanoids (e.g., PGE1, PGE3, PGI2) and arachidonic acid metabolites (e.g., prostacyclin A2), thereby exerting vasodilatory effects on endothelial cells and inhibiting platelet aggregation, both of which effects will advantageously decrease blood pressure in hypertension, inflammation and stroke; and,
7. Without intending to be limited by theory, it is believed likely that topical application of the instant compositions induce changes in fatty acid metabolism of subcutaneous adipose tissue which lead to decreased tissue production of undesirable inflammatory mediators, e.g., (PGE2), such as may be produced in mammary tissue at certain times during the menstral cycle.

Diet has not proven a reliable method for achieving stable changes in unsaturated $C_{18}$ fatty acid metabolism in a target tissue. In different objects, the invention provides compositions and methods which achieve the desired result in a target tissue by topical administration at a cutaneous site proximal to the target tissue. While certain effects of essential fatty acids on adipocytes may have been hypothesized from in vitro controlled experiments, to the inventors knowledge it has not been appreciated that topical administration of a mixture of unsaturated $C_{18}$ essential fatty acids could produce effects on adipocytes in a vascularized subcutaneous adipose tissue under physiological conditions.

All percentages describing the composition herein are weight/weight percentages. Fatty acids are described by their total number of carbon atoms (subscript) followed by the total number of double bonds, e.g., $C_{18:2}$ being a fatty acid consisting of 18 carbon atoms and two double bonds.

The following terms, as used herein, are intended to have meanings as defined below: namely, "Topical application", "applied topically", "topical administration" and "administered topically", are used interchangeably to mean the process of applying or spreading one or more compositions according to the instant invention onto the surface of the skin of a subject in need thereof.

"Subject in need thereof" is intended to mean a mammal, e.g., humans, domestic animals and livestock, having one or more indicia of disease or indicia of cosmetic need.

"Dermatologically acceptable composition" is intended to mean a composition which when applied topically to the skin of a host does not induce redness, swelling, pain, irritation or itching, or induce or elicit an antibody or cell mediated immune or allergic response.

"Safe and effective amount" is intended to mean that amount of the instant compositions which is sufficient to either: (i) ameliorate one or more symptoms of a disease or (ii) produce one or more positive desirable cosmetic effects; and, further, the subject composition when topically applied is not painful; does not elicit irritation, a skin reaction, inflammation or an allergic reaction.

"Indicia of a disease" is intended to mean a clinical symptom of disease as may be determined by a physician by palpation, visual observation, taking of a patient history and the like; with or without aid of automated or other laboratory test equipment. Representative symptoms of disease include increased body temperature, nausea, vomiting, tenderness, discomfort, pain, itching, swelling, redness, palpable subcutaneous lumps, painful lactation, menstrual breast pain (e.g., pre-, during and post-menstral) and the like. Representative clinical indicia of disease also include pathologic abnormalities visible by X-ray, Ultrasound, CatScan, NMR imaging and the like, e.g., shadows, vascularization, fibrous cysts, fibromas, cancer and the like. Representative examples of indicia useful for identifying subjects in need having cyclic mastalgia, benign breast pain, premenstrul breast pain and tenderness, swelling and discomfort lasting about 1 to about 14 days, fibrocystic disease, presence of nodules in breast tissues, presence of one or more cysts on palpation or mammogram, fibroadenoma, cancer and the like, are as set forth in Dixon et al. (1) and Ader et al. (2), incorporated herein by reference in their entirety.

"Inflammation" is intended to mean redness, swelling and pain, manifest histologically as leukocyte pavementing in capillaries, thinning of capillary endothelial cells and possible thinned or disrupted junctional complexes between endothelial cells. Inflammation is intended inclusively, to encompass a variety of tissues, e.g., cutaneous tissues of the integument, mammary tissues, loose connective tissue, joint tissues of patients with rheumatoid arthritis and the like.

"Cosmetic indicia of need" is intended to mean a desired visible improvement in skin and tissue appearance following one or more topical applications of one or more compositions according to the invention. Representative cosmetic effects include increasing desirable skin smoothness, oiliness and texture, suppleness, firmness, as well as, decreasing undesirable skin wrinkling and tactile discontinuities such as scarring and tissue sagging. Cosmetic effects are also intended to encompass desirable increase in the size or shape of a tissue, e.g., decreased tissue sagging, increased size firmness and suppleness and the like. Without intending to be limited by theory, it is presently believed likely that topical application of the instant compositions is effective over a period of about 1 to about 4 weeks to alter adipocyte triglyceride metabolism, resulting at the cellular level in an increase in adipocyte cell size. Recognizing first the effects of the instant topically applied compositions on breast adipose tissues, a variety of additional treatments are disclosed (below) for achieving cosmetic effects of decreased wrinkling and increased firmness in tissues with subcutaneous adipose tissue, e.g., amelioration of wrinkling and stretch marks in facial tissues, post-pregnancy abdominal skin and the like. Methods for measuring cosmetic indicia are known to those skilled in the art, e.g., tensile strength to compression forces, surface moisture, (as reflected in skin electrical capacitance measurements in a corneometer, Courage and Khazaka), and the like.

"Ameliorating" is intended to mean improvement in one or more indicia of disease or cosmetic indicia following topical application of one or more of the instant compositions. Amelioration is intended to include improvements in determinations made following either a therapeutic or a prophylactic topical application. Representative indicia in a therapeutic setting include a decrease in one or more clinical or cosmetic indicia, and in a prophylactic setting may include a decrease in the incidence (or risk) of developing the subject undesirable clinical or cosmetic indicia.

"$C_{16:0}$ fatty acid" is intended to mean a $C_{16}$ fatty acid having no double bonds, e.g., palmitic acid.

"$C_{16:1}$ fatty acid" is intended to mean a $C_{16}$ fatty acid having one double bond, e.g., palmitolenic acid.

"$C_{18:0}$ fatty acid" is intended to mean a $C_{18}$ fatty acid having no double bonds, e.g., stearic acid.

"$C_{18:1}$ fatty acid" is intended to mean a $C_{18}$ fatty acid having one double bond, e.g., oleic acid.

"Unsaturated $C_{18}$ fatty acid" is intended to mean one or more $C_{18}$ fatty acids selected from the group consisting of linoleic acid, α-linolenic acid, γ-linolenic acid, dihomo-γ-linolenic acid, conjugated linoleic acid and isomers thereof.

"Linoleic acid", abbreviated LA, is intended to mean a $C_{18:2}$ essential fatty acid two double bonds, i.e., at $C_9=C_{10}$ and $C_{12}=C_{13}$, as carbon atoms are numbered from the carboxyl terminus of the fatty acid.

"α-Linolenic acid", abbreviated α-LA and ALA, is intended to mean a $C_{18:3}$ essential fatty acid having three double bonds, i.e., $C_9=C_{10}$, $C_{12}=C_{13}$ and $C_{15}=C_{16}$ as numbered from the carboxyl terminal.

"γ-linolenic acid", abbreviated GLA, is intended to mean a $C_{18:3}$ fatty acid having three double bonds, i.e., $C_6=C_7$, $C_9=C_{10}$, $C_{12}=C_{13}$ as numbered from the carboxyl terminal. Gamma linolenic acids, as unsaturated fatty acids, are temperature and UV sensitive, oxidized and labile and unstable on storage in air.

"Conjugated linoleic acid", abbreviated CLA, is used to mean a $C_{18:2}$ fatty acid, including mixtures of isomers, and the cis-9, trans-11 CLA isomer and the trans-10, cis-12 isomer. Representative commercial preparations of CLA commonly consist of a mixture of isomers, predominantly 9-cis, 11-trans and 10-trans, 12-cis linoleic acids. CLA is a product of natural rumen fermentation and may be found in milk and muscle of ruminants and mammals (e.g. see 52,53).

"Cis $C_9$-trans $C_{11}$ CLA" is intended to mean a composition comprising greater than about 80%, preferably greater than about 90%, of the 9-cis, 11-trans isomer of CLA.

"Trans $C_{10}$-cis $C_{12}$ CLA" is intended to mean a composition comprising greater than about 80%, preferably greater than about 90%, of the 10-trans, 12-cis isomer of CLA. Recent reports disclose synthesis of individual CLA isomers, e.g., 8-cis/10-trans, 9-cis/11-trans-, 10-cis/12-trans- and 11-cis/13-trans octadecadienoate (54–56). CLA in plant oils, e.g., from transgenic plant species, are anticipated for use in the instant compositions.

"Dihomo-γ-linolenic acid", abbreviated DHGLA, is intended to mean a $C_{20:3}$ fatty acid having three double bonds, i.e., $C_8=C_9$, $C_{11}=C_{12}$, $C_{14}=C_{15}$ as numbered from the carboxyl terminal.

"Natural stable unsaturated $C_{18}$ fatty acid composition" is intended to mean an oil extract of a plant seed, nut, leaf and like as set forth further below. The subject oil is preferrably refined (e.g. alkaline water washed to remove free fatty acids) and optionally bleached (e.g., treated with adsorbants to remove color pigments) and deodorized (e.g., steam oil under vacuum to remove glycerides, pigments, fatty oxidation products and the like), but under conditions suitable for retaining unsaturated $C_{18}$ fatty acids, i.e., as disclosed further below. The subject oil preferably contains about 1.5-time to about 2-times more polyunsaturated fatty acids than saturated fatty acids, and preferably greater than about 40% of the fatty acids present in the oil are present as unsaturated $C_{18}$ fatty acids; and most preferably having greater than about 50% of the fatty acids present as unsaturated fatty acids. The subject composition additionally contains greater than about 40% of the fatty acids present as unsaturated linoleic ($C_{18:2}$), conjugated linoleic ($C_{18:2}$), α-linolenic ($C_{18:3}$) and/or γ-linolenic ($C_{18:3}$) fatty acids. "Stable" as used in respect to the subject unsaturated linoleic/linolenic composition is intended to mean AOM stability of about 15 hours, or greater than 3 months shelf storage stability as an oil at room temperature, in the cool and dark, without need for additional processing or formation of trans fatty acids. Representative examples of natural stable unsaturated $C_{18}$ compositions are disclosed in greater detail below.

"Arachidonic acid", abbreviated AA, is intended to mean a $C_{20:4}$ fatty acid having four double bonds, i.e., $C_5=C_6$, $C_8=C_9$, $C_{11}=C_{12}$, $C_{14}=C_{15}$ as numbered from the carboxyl terminal.

"Bioadhesive Carrier" is intended to mean a polymeric material that is particulate at room temperature, liquid at about 70° C. to about 90° C., acting as a diluent, dispersant and solvent for the instant cream compositions, having adhesive properties for skin, e.g., by binding to skin proteins, and capable of topical application and distribution such that an even distribution is achieved over a desired area of the skin, and further, so that a topically efficacious dosage of a $C_{18}$ fatty acid is delivered to subcutaneous adipose tissue at the subject site of topical administration. Representative carriers include a variety of acrylic homopolymers, preferably having molecular weights in of at least about $10^6$ gm/mole, with about $1.35\times10^5$ monomers/mole, each of which having a monomer molecular weights of about 72 gm/mole. Preferably, the instant carrier comprises a wax dispersed evenly in an aqueous phase. Preferably, the instant carrier comprises about 0.4% w/w to about 5.0% of the subject polyacrylate polymer, and most preferably, about 0.6% to about 1.4%. Representative examples of the instant bioadhesive polymeric carrier include commercial polymeric polyacrylic acids known in the art as 2-propenoic acid homopolymers, Carbomer 940, Carbomer 934P, Carbomer 934, Carbomer 1342, and polyacrylic acid polymeric derivative thereof having similar physical properties of melting point, solution viscosity and biological properties. The instant carrier may optionally comprise additives, extenders, fillers and the like capable of increasing the volume of the instant composition without interfering with delivery of a safe and effective dose of the instant $C_{18}$ fatty acid at the subcutaneous adipose tissues.

Embodiments of the invention provide a variety of formulations in which the amount and selection of a carrier may vary somewhat depending upon the intended topical site of treatment and intended method of delivery. For instance, for application to the skin of the hands and face, lotions may desirable while for delivery to breast and abdominal skin creams may be selected, while for other applications (e.g., to femoral skin) gels, sticks, sprays and ointments may be more desirable, and for facial uses pastes, mousses and cosmetic powders and gels may be selected for delivery (e.g., as solids, semi-solids, or liquid make-ups, including foundations, eye-make-ups, pigmented or non-pigmented lip treatments, e.g., lipsticks, and the like). Thus, a variety of carriers are envisaged for the instant compositions and these carriers may include vegetable and plant oils. Preferably, the subject carriers or bioadhesive carrier, are suspended or dissolved uniformly in a diluent.

"Diluent" is intended to mean the liquid in which the carrier (supra), or bioadhesive carrier (supra) is dispersed, dissolved, or otherwise incorporated at room temperature, or a temperature greater than room temperature. Nonlimiting examples of diluents include water, buffered aqueous solutions, organic hydrophilic diluents such as lower monovalent alcohols (e.g., $C_1$–$C_4$) and low molecular weight glycols and polyols, including propylene glycol, polyethylene glycol (e.g., Molecular Weight 200–600 g/mole), polypropylene glycol (e.g., Molecular Weight 425–2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Preferably, the diluent comprises water, ethanol, glycerol, sorbitol (as a stabilizer), propylene glycol (as an emulsifier, dispersant, surfactant and preservative for preventing fungal growth) and sodium borate and sodium ascorbyl phosphate (as a water soluble vitamin C). Preferably, the diluent comprises about 30% (w/w) to about 85% (w/w) water, most preferably about 40% to about 60% (w/w) water; about 4% (w/w) to about 24% (w/w) ethanol, most preferably about 10% to about 20%; about 0.08% (w/w) to about 10% (w/w) glycerol, most preferably about 0.1% to about 3% (w/w); about 0% (w/w) to about 1.2% (w/w) sorbitol (D-glucitol; as a thickener), most preferably about 0.5% to about 1.0% (w/w) sorbitol; about 2.0% (w/w) to about 10% (w/w) propylene glycol, most preferably about 2% to about 6% (w/w) propylene glycol; about 0 to about 0.1% (w/w) sodium borate and about 0.1 to about 5% (w/w) sodium ascorbyl phosphate, most preferably about 0.2% to about 1.5% (w/w); and, triethanolamine (trihydroxytriethanolamine) to achieve a final finished pH of about pH 5.0 to about pH 8.0, most preferably about pH6.5 to about pH 7.2.

Optionally, the diluent may include a penetration enhancing agent effective to increase the penetration of the final emulsion into subcutaneous tissues. In a presently preferred embodiment, the diluent contains about 0% (w/w) to about 1.2% (w/w), most preferably about 0.5% to about 1.2% (w/w) of imidurea as a penetration enhancing agent.

"Natural herbal anti-inflammatory agent" is intended to mean an agent which when isolated from a plant found in nature and then topically applied to a mammal is effective to inhibit redness, swelling and/or heat. Isolation from the subject plant may be accomplished in a variety of ways, e.g., by crushing to collect a plant oil, by water extraction, by alcohol extraction and the like. Representative examples of the natural herbal anti-inflammatory compounds include unpurified and substantially purified oils collected from chamomile species, e.g., *Chamomilla recutita*; from *Matricaria chamomilla L.*; from wormwood *Artemisia absinthium L.*; and from yarrow (*Achillea millefolium L*, Compositae). The subject natural anti-inflammatory oils contain one or more of the following compounds: namely, an alpha-bisabolol, a hydroxy-bisabolol; a levomenol, a 6-methyl-2-(4-methyl-3-cyclohexen-1-yl)-5 hepten-2-ol (alpha bisbolol), a tiglic acid esters such as (E)-2-methyl-2-butenoic acid and an azulene, e.g., chamazulene (7-ethyl-1, 4-dimethylazulene).

"Natural weak analgesic agent" is intended to mean an agent which when isolated from a plant found in nature and then topically applied to a mammal is effective to inhibit pain. The subject natural weak analgesic agent is capable of binding a vanillin receptor in a neural cell and blocking a potassium current in that cell. Representative methods for determining that a compound is so active are known in the art of neurobiology, e.g., see citation 57, below. Representative compounds so active include, vanillin (4-hydroxy-3- methyoxybenzaldehyde, methylprotocatechuic aldehyde) a metabolic product of curcumin; compounds containing the homovanillin ring; and derivatives of capsaicinoids (e.g., capsaicin) which are not skin irritable.

"Natural estrogenic agent" is intended to mean an agent which when isolated from a plant found in nature and then topically applied to a mammal is effective to promote the synthesis of estrogen. Representative tests for determining that the subject compound is so estrogenic are known in the art, e.g., see citation 58. Representative compounds so active include alkyl-hydroxy-benzoate derivatives such as methylparaben, propylparaben and butyl-paraben. Instruction is given that while the subject compounds are inactive orally, when administered topically or subcutaneously they evoke estrogenic responses that are about 100,000 fold lower than a similar dosage of estrogen.

Embodiments of the invention provide compositions capable of ameliorating one or more clinical or cosmetic indicia in a patient in need thereof by delivering a safe and effective dosage of an unsaturated $C_{18}$ fatty acid to subcutaneous adipose tissue at one or more topical sites of administration. The instant compositions comprise a safe and effective amount of the subject unsaturated $C_{18}$ fatty acid which when administered topically as a dermatologically acceptable composition effects penetration of the unsaturated $C_{18}$ fatty acid through the skin and into subcutaneous tissues containing adipocytes. The concentration and rate of delivery of the unsaturated $C_{18}$ fatty acids at the subcutaneous adipose tissues is effective to produce an ameliorating effect on one or more indicia of disease and/or one or more indicia of cosmetic need.

The instant compositions contain agents effective to promote binding of the carrier to the skin, and to promote penetration of a $C_{18}$ fatty acid into skin and subcutaneous adipose tissue in a manner effective to achieve a safe and effective dose. "Penetrant", as used herein, is intended to mean an agents which promotes skin penetration. Representative penetrants include protein denaturants, e.g., urea (carbonyldiamide), imidurea (supra), palmitate, optional isoproyl myristate, propylene glycol (as a co-solvent and/or penetration enhancing agent) and nonionic detergents, e.g., Brij 98/99 Oleyl esters such as Brij 98/99, Stearyl ethers such as Brij 721 ($C_{18}E_{21}$), Brij 78 ($C_{18}E_{20}$), Brij 76 ($C_{18}E10$), Brij 96 ($C_{18-1}E_{10}$) and Brij 721 ($C_{18}E_{21}$), or mixtures thereof. Preferably, the instant composition contains about 1.0% (w/w) to about 6.0% (w/w) urea, most preferably about 1% to about 3% (w/w) urea; about 0% (w/w) to about 4% (w/w) triethanolamine (i.e., to achieve desired pH), most preferably about 0% to about 2% (w/w) triethanolamine; and, about 0.5% (w/w) to about 2% (w/w) Brij 99, most preferably about 0.5% to about 1.5% (w/w) Brij 99. Other representative examples of nonionic surfactants which may prove useful include polyoxyethylene glycol esters of $C_{18}$ saturated fatty acids; PEG fatty acid esters; ethoxylated fatty acid esters, and macrogol fatty acid esters of the general formula $RCOO(CH_2CH_2O)_nH$ or $RCOO(CH_2CH_2O)_nOCR$, wherein R comprises a long chain alkyl group or a mixture of different alkyl groups, preferably comprising a $C_{18}$ alkyl chain; and wherein n comprise is an integer 20 or 21.

In other embodiments, the invention provides compositions for topically administering a safe and effective dosage of a stable hydrophilic:hydrophobic cream consisting of a $C_{16:0}$, $C_{16:1}$, $C_{18:0}$ and/or $C_{18:1}$ fatty acids as penetrants, emolients and stabilizers in emulsion with one or more of an unsaturated $C_{18:2}$, $C_{18:3}$, $C_{20:3}$ or $C_{20:4}$ fatty acids, i.e., as medicinal agents.

Preferably, the instant hydrophilic:hydrophobic cream emulsion comprises about 5% (w/w) to about 25% (w/w) of the penetrant/emollient fatty acids (i.e., $C_{16:0}$, $C_{16:1}$, $C_{18:0}$ and/or $C_{18:1}$), most preferably about 5% (w/w) to about 15% (w/w). In one illustrative composition, i.e., set forth in the EXAMPLES section below, cottonseed oil, isopropyl palmitate and Brij 99 are used. Palmitic ($C_{16:0}$) and steric ($C_{18:0}$), i.e., fatty acids present in cottonseed oil at about 26% of fatty acids present, thus contribute 5.7% (w/w) to the final composition; oleic acid ($C_{18:1}$) in the cottonseed oil at about 18% contributes 4% (w/w); and additional fatty acid additives isopropyl palmitate ($C_{16:0}$) 4.5% (w/w) and Brij 99 ($C_{18:0}$) at 1% (w/w), giving a total for the cream of about 15.2% (w/w).

Preferably, the instant hydrophilic:hydrophobic cream emulsion additionally comprises about 3% (w/w) to about 30% (w/w) of the medicinal $C_{18:2}$, $C_{18:3}$, $C_{20:3}$, $C_{20:4}$, $C_{22}$ and/or $C_{24}$ fatty acids, most preferably about 5% (w/w) to about 15% (w/w). In illustrative compositions, i.e., set forth in the EXAMPLES section below, cottonseed oil, borage oil, CLA and GLA are used. In one example, LA ($C_{18:2}$) present in cottonseed oil at 50–52% of the total oil composition contributes 11.4% (w/w) to the final composition while ALA ($C_{18:3}$) in the same oil at 0.3% contributes 0.1%, with additional GLA ($C_{18:3}$) being added to supplement the composition, i.e., 0.05% (w/w) bringing the total desired medicinal fatty acids to a total of 11.55% (w/w).

Representative $C_{16}$ fatty acid derivatives include e.g., isopropyl palmitate ($C_{16:0}$) and palmitoleic ($C_{16:1}$). Representative $C_{18}$ saturated fatty acids include e.g., oleic acid ($C_{18:1}$), stearic acid ($C_{18:0}$) and Brij 99 (polyoxyethylene glycol esters of $C_{18:0}$ fatty acids). —Representative unsaturated $C_{18:2}$ fatty acids include LA, CLA and derivatives thereof; Representative $C_{18:3}$ fatty acids include ALA, GLA and derivatives thereof; and, representative $C_{20:3}$ and $C_{20:4}$ fatty acids include DHGLA, AA and derivatives thereof. Representative vegetable oils containing the subject unsaturated $C_{18}$ fatty acids in mixtures include: oils from the seeds of cultivated varieties of *Gossypium herbaceum L.* and other species of Gossypium, e.g. cottonseed oil and the like. Representative $C_{20}$ and $C_{22}$ fatty acids in mixture include e.g., fatty acids present as mixtures of esters extracted from ground or crushed seeds of *Simmondsia chinensis* and *S. californica Nutt. Buxaceae*, and $C_{20}$ and $C_{22}$ straight chain monoethylene acids and alcohols in the form of esters, e.g., similar to sperm whale oil. Preferably, $C_{20}$ and $C_{22}$ fatty acids comprise a mixture of fatty acids substantially equivalent to that present in Jojoba oil. The instant components preferably constitute a stable emulsion wherein certain of the constituent fatty acids may serve as surfactants, i.e., improving the stability and quality of dispersion of the components in the emulsion.

Unsaturated fatty acids are unstable, particularly susceptible to photo oxidation in light and air. In other embodiments the invention provides stable emollient compositions containing unsaturated $C_{18:1}$, $C_{18:2}$, $C_{18:3}$, $C_{20:3}$, $C_{20:4}$, $C_{20}$ and/or $C_{22}$ fatty acids for topical administration containing, in addition, the following: namely, (i) anti-microbial compounds, e.g., parabens; (ii) stabilizers, e.g., sorbitol; (iii) antioxidants, e.g., α-tocopherol and sodium ascorbyl phosphate; and, (iv) in a stable emulsion comprising both a hydrophilic phase and a hydrophobic phase. The latter emulsion is effective to minimize oxidation of the unsaturated fatty acids. Preferably, the hydrophilic phase constitutes the diluent for the carrier, vehicle and penetrant (supra); and, the hydrophobic phase, and optional alcohol, comprise the saturated $C_{16:0}$ fatty acids, the unsaturated $C_{18:1}$, $C_{18:2}$, $C_{18:3}$, $C_{20:3}$, $C_{20:4}$ and/or $C_{22}$ fatty acids and the saturated $C_{18:0}$ fatty acids, the natural anti-inflammatory agent, the natural analgesic agent and the natural estrogenic agent. Preferably, the subject carrier is dissolvable, or uniformly dispersible, in the hydrophilic phase; and the saturated $C_{16:0}$, saturated $C_{18:0}$ and unsaturated $C_{18:1-3}$, $C_{20:3}$ and $C_{20:4}$ fatty acids and the $C_{20}$ and $C_{22}$ fatty acids are uniformly dispersible in the hydrophobic phase, e.g. forming a oil:water emulsion or water:oil emulsion. Preferably, the instant emulsion comprises a "dispersed phase". The term "dispersed phase" is intended to mean that the hydrophobic phase exists as small particles or droplets that are suspended in and surrounded by a continuous hydrophilic phase constituting an internal or discontinuous phase. The latter discontinuous phase provides beneficial restricted access to atmospheric air, thereby limiting oxidation of the unsaturated fatty acids in the dispersed phase and providing stable properties to the instant compositions. Optionally, in other embodiments the instant emulsion may comprise a gel network, such as known to those in the cosmetics arts, e.g., as described in G. M. Eccleston, Application of Emulsion Stability Theories to Mobile and Semisolid O/W Emulsions, Cosmetics & Toiletries, Vol. 101, November 1996, pp. 73–92, incorporated herein by reference. The hydrophobic phase component may be derived from animals, plants, or petroleum and may be natural or synthetic (i.e., man-made). Preferred hydrophobic components occur in plants as substantially water-insoluble oils, most preferably, as essentially water-insoluble oil. Preferred hydrophobic components are those having a melting point of less than about 20° C. to about 35° C. under about one atmosphere of pressure.

In a preferred embodiment, the unsaturated $C_{18:2}$ and $C_{18:3}$ fatty acid constituents of the instant emollients consists of a natural stable unsaturated $C_{18:2}$ and $C_{18:3}$ fatty acid oil. The subject natural stable oils most preferably consists of about 1.6- to about 2-times more polyunsaturated fatty acids (e.g., LA, ALA, GLA, CLA) than saturated fatty acids (e.g., palmitic, stearic) and also contain less than about 3% of cholesterol and triglycerides. "Natural" is intended to mean that the subject oil may be prepared from a source present in nature, e.g., vegetables, seeds, beans and the like. Preferably, the subject natural oil has greater than about 40% of the fatty acids present as unsaturated fatty acids; and most preferably greater than about 50% of the fatty acids present are unsaturated fatty acids. Preferably, the subject natural oil additionally contains greater than about 40% of the fatty acids present as unsaturated $C_{18:2}$ and/or $C_{18:3}$, and most preferably greater than about 50% of the fatty acids present are LA, ALA, GLA and/or CLA. "Stable" as used in respect to the subject natural oil is intended to mean AOM stability (active oxygen stability, hours of heating until a peroxide value of 100 milliequivalent units is reached) of about 15 hours, or greater than 3 months shelf storage stability as an oil at room temperature, in the cool and dark, without need for additional processing. Representative examples of natural stable oils consisting of unsaturated $C_{18:2}$ and $C_{18:3}$ fatty acids include the following vegetable cooking and salad oils: namely, hemp oil, chia oil, kukui oil, flax oil, soybean oil, cottonseed oil, walnut oil, wheat germ oil, evening primrose oil, safflower oil, grape oil, canola oil, sunflower seed oil, blackcurrant oil, borage oil, corn oil, sesame oil and mixtures thereof. Preferably, the natural stable unsaturated $C_{18:2}$ and $C_{18:3}$ fatty acid compositions are selected from the group of natural stable oils consisting of: cottonseed oil, hemp oil, chia oil, kukui oil, flax oil, soybean oil, walnut oil, wheat germ oil, evening primrose oil, borage oil and mixtures thereof. The subject natural stable oils are preferably prepared by processing seed kernels, nuts, beans and the like using cold (i.e., less than about 50° C.) batch pressing, crushing, grinding or milling, hydraulic pressing, or cold in-line cooling low resistance expeller pressing. The resultant oils may optionally be (i) "refined" to remove certain free fatty acids, chlorophylls, chromophores and the like (e.g., by alkaline treatment, filtration or centrifugation, water washing) and (ii) "winterized" (e.g., chilled and filtered to remove higher melting point fats, waxes, sterols, styrenes, phospholipids and the like) or "degummed" (e.g., washed with water to remove phospholipids). However, the subject oils are not hydrogenated and not heated (e.g., not deodorized at 200° C. in steam under vacuum). Preferably, the subject natural oils do not contain preservatives or defoaming agents as additives. The subject vegetable oils are commonly stable and free of trans fatty acids. Preferred melting points for the subject oils are in the range of about −15° C. to about 0° C.

In other embodiments, the invention provides a safe and effective dosage of a natural herbal anti-inflammatory compound.

In other embodiments, the invention provides a composition for topical administration of a safe and effective dosage of an optional fragrance or of a natural weak analgesic agent capable of binding a vanillin receptor in a neural cell as evidenced e.g., by blocking a potassium current in that cell. Representative methods for determining that a compound is so active are known in the art of neurobiology, e.g., see citation 57, below.

In other embodiments, the invention provides a composition for topical administration of a safe and effective dosage of a preservative or of one or more compounds capable of stimulating estrogen synthesis in an adipocyte. Preferably, the instant compositions comprise about 0% (w/w) to about 1.0% (w/w), most preferably about 0.04% to about 0.12% % of a paraben. The subject parabens are selected from the group consisting of methylparaben, ethylparaben, propylparaben, butylparaben and mixtures thereof. Preferably, the parabens are selected from methylparaben, propylparaben and butylparaben.

Embodiments of the invention provide safe and effective compositions for topical administration comprising all of the following: namely, an essential unsaturated $C_{18}$ fatty acid (e.g., GLA or CLA), a natural anti-inflammatory agent (e.g., bisabolol), a natural estrogenic agent (e.g., a paraben) and a natural analgesic agent (e.g., a vanillin).

In certain embodiments, the invention provides compositions containing GLA and/or CLA at a concentration effective to exert antibacterial effects. "Antibacterial effects" is intended to mean that the subject compositions are effective to either inhibit the growth of a resident or pathogenic skin bacteria, to decrease expression of a toxin by the subject bacteria, or to effect a change in the antibiotic sensitivity of the subject bacteria, e.g., by curing to remove one or more plasmids carrying antibiotic resistance genes. That the subject bacteria has been affected in this manner by the subject composition may be determined according to methods known to those skilled in the art, e.g., for growth inhibition see Raychowdhury et al. (59), Altenbern et al., (60) or Fyfe, et al. (61); for altering antibiotic resistance see Butcher et al. (62).

In other embodiments, the invention provides a fragrant oil-in-water cream emulsion of $C_{18}$ fatty acids, wherein the fragrance is contributed to the composition by Ylang-Ylang oil (Cananga oil, from flowers of *Cananga odorata*); and most preferably vanilla extract.

Embodiments of the invention provide delayed release compositions capable of producing a slow release of essential unsaturated $C_{18}$ fatty acids at a site of topical application by providing to a normal resident skin bacterium a source of saturated $C_{18}$ fatty acids in a composition capable of promoting all of: (i) bacterial fatty acid metabolism, (ii) production of $C_{18}$ unsaturated fatty acids and (iii) release from the bacterium of linoleic acid, α-linolenic acid and/or γ-linolenic acid. "Skin bacterium" is intended to mean an aerobic or anaerobic bacterium capable colonizing a skin location including a hair follicle, the cornified layer, a sebaceous gland or a milk duct. Representative examples of skin bacteria include bifidobacteria, e.g., *Bifidobacterium longum, Bif adolescentis, Bif. pseudolongum* and *Bif infantis*; Bacteroides, e.g. *Bacteroides thetaiotaomicron* and *Bact. vulgatus*; desulfovibrio, e.g., *Desulfovibrio desulfuricans*, streptococcus, e.g., *Lactobacillus acidophilus* and *Streptococcus salivarius*; staphylococcus, e.g., *S. aureus, S. hyicus, S. intermedius*, and *S. epidermidis*; and *Helcococcus kunzii*. Beneficial synthetic products released by skin bacteria in response to topical application of the instant compositions may include: $C_{18}$ fatty acids (bifidobacteria); i-$C_{15:0}$, $C_{16:0}$ and i-$C_{17:1}$ (iso; desulfovibrio) fatty acids; esterified $C_{15-19}$ fatty acids (products of fatty acid modifying enzyme of *S. aureus*, 61); and unsaturated fatty acids (streptococcus, 63). While not wishing to be tied to any particular mechanism of action, at the levels applied $C_{18}$ fatty acids, i.e., Brij 99, and $C_{16}$ fatty acids, i.e., palmitate, are biosynthetic sources useful to certain skin bacteria; glycerol stimulates bacterial fatty acid metabolism; parabens (i.e., methyl and propylparaben) and GLA inhibit bacterial growth; with resultant lowlevel release from the bacteria of a safe and effective dose of essential unsaturated $C_{18}$ fatty acids at the site of topical application.

The instant compositions may optionally contain a wide variety of additional components intended to improve the overall desirability, visual appearance, physical properties and/or physical feel, but provided that such optional additives are physically and chemically compatible with the essential components described herein (supra), and do not unduly impair stability, safety or efficacy. Optional additives may be dispersed, dissolved or the like in the carrier of the present compositions. Optional additives include possible aesthetic agents, (e.g., absorbents including oil absorbents in the form of cosmetic clays and polymeric absorbents), abrasives, anti-caking agents, antifoaming agents, additional anti-microbial agents, binders, buffering agents, bulking agents, cosmetic biocides, additional denaturants and penetrants (supra), cosmetic astringents, drug astringents, external analgesics, film formers, opacifying agents, fragrances, perfumes, pigments, colorings, skin soothing agents, pH adjusters, chelating agents, UV light absorbing agents, plasticizers, preservatives, preservative enhancers, depilating agents, desquamation agents and exfoliants, collagens and breakdown products thereof, film-forming agents and the like. Representative examples of such materials are disclosed in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962–1965); and in The Handbook of Cosmetic Science and Technology, 1st Ed. Knowlton & Pearce (Elsevier 1993).

In other embodiments, compositions suitable for topical administration according to the methods of the invention include, but are not limited to lotions, gels, pastes, mousses, creams, cosmetic cakes, foundations, powders, blushers, rouge, ointments, skin cleansers, emollient liquids and the like. Composition known in the art include those disclosed in Sagarin, Cosmetics, Science and Technology, 2nd Edition, Vol. 1, pp. 32–43 (1972), incorporated herein by reference; Kowcz et al., U.S. Pat. No. 4,800,197; McCutcheon's Detergents and Emulsifiers, North American Edition (1986); and Barford et al., U.S. Pat. No. 4,835,148. Typically the foundation, paste, cake and the like is applied to an area of the skin where amelioration of a cosmetic indicia of need is located, e.g., a scar, wrinkle, line or sagging tissue. Alternative composition for use according to the methods of the invention also include compositions having a hydrophilic and hydrophobic phase. Non-limiting examples of suitable non-natural hydrophobic phase components include: (i) a non-toxic and non-carcinogenic mixtures of liquid hydrocarbons obtained from petroleum (64, 65); (ii) a non-toxic, non-carcinogenic colloidal system of nonstraight-chain solid hydrocarbons and high-boiling liquid hydrocarbons in which most of the liquid hydrocarbons are micellar (64, 66, 67); (iii) non-toxic and noncarcinogenic straight and branched chain hydrocarbons having from about 7 to about 40 carbon atoms, e.g., dodecane, isododecane, squalane, cholesterol, hydrogenated polyisobutylene, docosane (i.e. a $C_{22}$ hydrocarbon), hexadecane, isohexadecane (Permethyl.RTM 101A, Presperse, South Plainfield, N.J.), and the like; (iv) non-toxic and non-carcinogenic $C_{1-30}$ alcohol esters of $C_{1-30}$ carboxylic acids and of $C_{2-30}$ dicarboxylic acids, including straight and branched chain materials as well as aromatic derivatives (e.g., diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenrate, dioctyl maleate, dioctyl sebacate, diisopropyl adipate, cetyl octanoate, diisopropyl dilinoleate. (v) non-toxic and non-carcinogenic mono-, di- and triglycerides of $C_{1-30}$ carboxylic acids, e.g., caprilic/capric triglyceride, PEG-6 caprylic/capric triglyceride, PEG-8 caprylic/capric triglyceride. (vi) non-toxic and non-carcinogenic alkylene glycol esters of $C_{1-30}$ carboxylic acids, e.g., ethylene glycol mono- and di-esters, and propylene glycol mono- and di-esters of $C_{1-30}$ carboxylic acids e.g., ethylene glycol distearate; (vii) non-toxic and non-carcinogenic propoxylated and ethoxvlated derivatives of the foregoing materials; and (viii) non-toxic and non-carcinogenic $C_{1-30}$ mono- and poly-esters of monosaccharides and oligosaccharides. Examples of liquid esters that may prove useful in the hydrophobic phase include glucose tetra-oleate; glucose tetra-esters of soybean oil fatty acids (unsaturated); mannose tetra-esters of mixed soybean oil fatty acids; galactose tetra-esters of oleic acid; arabinose tetra-esters of linoleic acid; xylose tetra-linoleate; galactose penta-oleate; sorbitol tetra-oleate; sorbitol hexa-esters of unsaturated soybean oil fatty acids; xylitol penta-oleate; sucrose tetra-oleate; sucrose pentaoletate; sucrose hexa-oleate; sucrose hepta-oleate; sucrose octa-oleate; and mixtures thereof.

In other embodiments, compositions suitable for topical administration according to the methods of the invention include, compositions having alternative carriers. Examples of alternative carriers include cross-linked polymeric compounds containing one or more monomers derived from acrylic acid, substituted acrylic acids, and salts and esters of these acrylic acids and the substituted acrylic acids, wherein the cross-linking agent contains two or more carbon-carbon double bonds and is derived from either (i) an acrylic acid homopolymeric polyhydric alcohol, e.g., crosslinked homopolymers of acrylic acid monomer or derivative thereof (e.g., $C_{1-4}$ alkyl, —CN, or —COOH substituted), where the acrylic acid has substituents at the two and three carbon positions (e.g., acrylic acid, methacrylic acid, ethacrylic acid, and mixtures thereof); or (ii) a cross-linked acrylate copolymer having both an acrylic acid monomer (or derivative thereof) and a $C_{1-4}$ alcohol acrylate ester monomer (or derivative thereof), and a second monomer which is a long chain alcohol (e.g. $C_{8-40}$) acrylate ester monomer (or derivative thereof), e.g., acrylic acid, methacrylic acid, ethacrylic acid, and mixtures thereof. Combinations of the latter two types of polymers are may also prove useful in certain compositions for use according to the treatment methods of the invention.

Embodiments of the invention provide methods for ameliorating one or more indicia of disease activity (supra) in a subject in need thereof, or alternatively, for ameliorating one or more indicia of cosmetic need (supra). The instant methods include both prophylactic and therapeutic protocols for treatments of conditions in man and domestic animals.

The methods of the invention find use in treatment of a variety of pathological conditions. For example, embodiments of the invention find us in treatment of cancer, dermatologic diseases, arthritis, inflammatory diseases and the like. The subject in need of treatment will generally exhibit one or more indicia of disease: for example, premenstral pain; inflammation; one or more fibroid cysts or lipid cysts; post-menopausal estrogen insufficiency; cyclic mastalgia; benign breast pain; premenstral syndrome including premenstral breast pain, tenderness, swelling and discomfort lasting about 1 to about 14 days; fibrocystic disease e.g., with nodules in breast tissues or one or more cysts on palpation or mammogram; fibroadenoma; carcinoma; tissue effects of diabetes including decreased blood flow and peripheral neuropathy; impaired fertility; low breast milk production; high tissue blood pressure or platelet aggregation in the microvasculature of an adipose tissue; menopausal hot flashes; skin and mucous membrane complications of Sjogren's autoimmune syndrome; skin and neural complications of shingles (Herpes zoster infection); rheumatoid arthritis; and the like. Alternatively, the subject in need will generally exhibit one or more indicia of a cosmetic need: for example, tissue sagging; undesirable scarring, skin wrinkles or lines; loss of cutaneous tissue tension or volume; lack of tissue firmness; psoriasis; dermatitis; skin disorders such as atopic dermatitis, scaly itchy skin; eczema; splitting fingernails; or, dryness of skin associated with aging and the like. Generally, indicia of cosmetic need include undesirable features of: (i) a cutaneous keratinized epithelium, i.e., the layers composing the skin, (e.g., wrinkles, lines, sagging, psoriasis, dermatitis, atopic dermatitis, scaly itchy skin, eczema, scars, and age related dryness of skin); or (ii) a cornified epithelium, i.e., the nails of the toes and fingers, (e.g., splitting finger or toe nails, discolored, ridged, grooved and irregularly shaped nails resulting from age, nutrition, cancer chemotherapy, and the like), and epithelium of the cornea (e.g., in cataract); or (iii) an undesirable feature of a mammary gland and an undesirable feature of a tissue containing adipose cells, (e.g., loss of cutaneous tissue tension, tissue sagging, decrease in tissue volume, lack of tissue firmness and lack of tissue fullnesss), such as may result from complications of aging, cancer cachexia, cancer chemotherapy, starvation, malnutrition or extreme or severe dieting.

Generally the instant methods will be effective to lessen the severity of one or more indicia of clinical or cosmetic need. "Amerliorate", used herein is intended to mean 'to make better', in this case decreasing the severity of one or more clinical indicia of disease or making improvements in a cosmetic indicia of need. The subject decrease in severity may be measured visually, (e.g. by taking the dimensions of a tissue or observing its properties), by palpation, or using instrumentation such as X-ray mammography, ultrasound, NMR imaging, skin electrical conductance, tension and resistance to deformation meters and the like. Commonly, the instant methods and compositions when topically administered are effective to induce a metabolic change in a subcutaneous adipose tissue. For example, a change in fatty acid metabolism in the tissue so-treated may result in measurable changes in glucose metabolism and synthesis of prostaglandin and arachidonate metabolites. Changes in metabolism of tissue so-treated in humans and domestic animals may be measurable, e.g., using calorimetry, doppler blood flow, infrared, NMR imaging and the like. Alternatively, the effects of the instant compositions, and constituents therein, may be evaluated in tissue culture using primary cultures of adipocytes, endothelial cells and epithelial cells.

The instant emollient compositions may be administered topically to any available cutaneous surface including e.g. face, hands, arms, legs, feet, abdomen and breasts with the underlying subcutaneous adipose tissue receiving benefit of the medication thus administered.

EXAMPLE 1

Preparations for Topical Administration

A series of nine illustrative cream emulsions according to the instant invention were prepared as follows by combining Phase-A, i.e., consisting of a carrier, with Phase-B, i.e., a vehicle and penetrant and Phase-C, i.e., a hydrophobic phase containing a mixture of saturated $C_{16}$ fatty acids, saturated and unsaturated $C_{18}$ fatty acids and $C_{20-22}$ fatty acids.

Preparation: Representative oil-in-water emulsion cream are prepared e.g. according to formulations in TABLE A, on the following page. All components are grade USP, or better.

TABLE A

ILLUSTRATIVE PREPARATIONS #1–10

| Component | PREPARATION (Weight in Grams) | | | | | | | | |
|---|---|---|---|---|---|---|---|---|---|
| | #1 | #2 | #3 | #4 | #5 | #6 | #7 | #8 | #9 |
| Phase A: Carrier | | | | | | | | | |
| Water | 43.3 | 48.9 | 35.0 | 43.00 | 35.00 | 38.5 | 35.0 | 38.75 | 37.25 |
| Carbomer 940 | 0.80 | 0.80 | 0.80 | 0.80 | 0.80 | 0.80 | 0.80 | 0.80 | 0.80 |

TABLE A-continued

ILLUSTRATIVE PREPARATIONS #1–10

PREPARATION (Weight in Grams)

| Component | #1 | #2 | #3 | #4 | #5 | #6 | #7 | #8 | #9 |
|---|---|---|---|---|---|---|---|---|---|
| Phase B: Vehicle/Penetrant | | | | | | | | | |
| Water | 14.43 | 14.48 | 8.43 | 14.48 | 8.43 | 8.43 | 8.43 | 8.43 | 8.43 |
| Urea | 2.95 | 2.95 | 2.00 | 2.95 | 2.95 | 2.95 | 2.95 | 2.95 | 2.95 |
| Imidurea | 0.05 | 0.05 | 1.00 | 0.05 | 0.05 | 0.05 | 0.05 | 0.05 | 0.05 |
| Sorbitol | 1.00 | 1.00 | 1.00 | 1.00 | 1.00 | 1.00 | 1.00 | 1.00 | 1.00 |
| Sodium borate | 0.05 | 0.05 | 0.05 | 0.05 | 0.05 | 0.05 | 0.05 | 0.05 | 0.05 |
| Sodium ascorbyl phosphate | 0.26 | 0.26 | 0.26 | 0.26 | 0.26 | 0.26 | 0.26 | 0.26 | 0.26 |
| Phase C: Hydrophobic Phase | | | | | | | | | |
| Cottonseed Oil*: | 0.00 | 0 | 22.00 | 0.00 | 22.00 | 21.0 | 17.05 | 17.0 | 17.0 |
| $C_{18:2}$ LA | 0 | 0 | [11.2] | 0 | [11.2] | [11] | [8.9] | [8.8] | [8.8] |
| $C_{18:3}$ ALA | 0 | 0 | [0.07] | 0 | [0.07] | [0.06] | [0.05] | [0.05] | [0.05] |
| $C_{18:1}$ Oleic | 0 | 0 | [3.96] | 0 | [3.96] | [3.8] | [3.07] | [3.06] | [3.06] |
| Ethyl Alcohol | 10.00 | 7.00 | 15.00 | 10.00 | 15.00 | 12.0 | 20.00 | 5.00 | 12.0 |
| Isopropyl Alcohol | 6.00 | 3.50 | 4.50 | 5.00 | 4.50 | 3.00 | 2.00 | 6.00 | 5.00 |
| Propylene Glycol | 6.00 | 10.00 | 4.00 | 7.00 | 4.00 | 5.50 | 5.00 | 10.00 | 5.00 |
| Bisabolol | 2.00 | 2.00 | 2.00 | 2.00 | 2.00 | 2.00 | 2.00 | 2.00 | 2.00 |
| Triethanolamine | 1.00 | 0.80 | 1.75 | 1.20 | 1.75 | 1.25 | 0.25 | 0.05 | 1.00 |
| Brij99 | 1.00 | 1.00 | 1.00 | 1.00 | 1.00 | 1.00 | 1.00 | 1.00 | 1.00 |
| α-tocopherol | 0.10 | 0.10 | 0.10 | 0.10 | 0.10 | 0.10 | 0.10 | 0.10 | 0.10 |
| Glycerin | 0.10 | 0.10 | 0.10 | 0.10 | 0.10 | 0.10 | 0.10 | 0.10 | 0.10 |
| Methylparaben | 0.05 | 0.05 | 0.05 | 0.05 | 0.05 | 0.05 | 0.05 | 0.05 | 0.05 |
| Propylparaben | 0.05 | 0.05 | 0.05 | 0.05 | 0.05 | 0.05 | 0.05 | 0.05 | 0.05 |
| $C_{18:3}$ GLA | 0.00 | 0.05 | 0.05 | 0.05 | 0.05 | 0.05 | 0.00 | 0.05 | 0.05 |
| Fragrance: Vanilla | 0.86 | 0.86 | 0.86 | 0.86 | 0.86 | 0.86 | 0.86 | 0.86 | 0.86 |
| $C_{18:2}$ CLA | 5.00 | 6.00 | 0 | 0.00 | 0.00 | 1.00 | 3.00 | 0.00 | 2.00 |
| Borage Oil:** | 5.00 | 0.00 | 0 | 10.00 | 0.00 | 0.00 | 0.00 | 5.00 | 3.00 |
| $C_{18:2}$ LA | [2.75] | [0] | [0] | [5.50] | [0] | [0] | [0] | [2.75] | [1.65] |
| $C_{18:3}$ GLA | [1.25] | [0] | [0] | [2.50] | [0] | [0] | [0] | [1.25] | [0.8] |
| TOTAL: | 100 g | 100 g | 100 g | 100 g | 100 g | 100 g | 100 g | 100 g | 100 g |

*LA, linoleic acid is equal to about 52% of fatty acids present in cottonseed oil; ALA, α-linolenic acid is equal to about 0.3% of fatty acids present in cottonseed oil; Oleic, is equal to about 18% of fatty acids present in cottonseed oil; the remainder of fatty acids present in cottonseed oil (i.e., about 26%) being palmitic and stearic acids.
**LA, linoleic acid is equal to about 55% of fatty acids present in borage oil; GLA, γ-linolenic acid is equal to about 25% of fatty acids present in borage oil;

The following illustrative preparative method is e.g. used to prepare about 1 kg of an emollient:

Vessels A, B and C can be established simultaneously.

In Vessel A (e.g., a 1000 mL beaker), 350 g of water is added and the vessel is placed on a hot plate equipped with an over head stirrer. Heat is slowly applied and 8 g of carbomer 940 is added slowly to Vessel A with stirring as the temperature is brought to about 50° C. to about 55° C.

In Vessel B (e.g., a 250 mL beaker), 84.3 g of water is added and then the following constituent components are added slowly with stirring: namely, urea (20 g), imidurea (10 g), sorbotol (10 g), sodium borate (0.5 g) and sodium ascorbyl phosphate (2.6 g). Stirring is continued at room temperature until the components are dissolved.

In Vessel C (e.g., an 800 mL beaker), 220 g of cottonseed oil are added followed by ethanol (150 g), isopropyl palmitate (45 g), propylene glycol (40 g), bisabolol (20 g), triethanolamine (17.5 g), brij 99 (10 g), vitamin E (1 g), glycerin (1 g), methylparaben (0.5 g), propylparaben (0.5 g), γ-linolenic acid (0.5 g) and fragrance (8.6 g). The component mixtures is then heated with stirring to about 50° C. to about 55° C. until the components are fully dissolved.

When uniform melts and solutions are achieved in all three vessels heat is removed, and the contents of Vessel B are then added to Vessel A with stirring (overhead stirrer), followed by the contents of Vessel C. Stirring is continued until uniformity of the cream is reached and the cream is allowed to reach room temperature.

EXAMPLE 2

Treatments of Swelling and Pain

Monthly female changes in estrogen and progesterone trigger mestration but often also result in swelling, redness, tenderness and pain in breast tissues. A study was conducted to determine the effects of emollient composition of EXAMPLE 1 (Preparation #3) on premenstrual breast pain, swelling and tenderness.

Study Inclusion Criteria: Patients were asked to complete a short medical history. Inclusion criteria included record of pre-menstral (and/or during menstration) breast pain and/or evidence of pain associated with fibroid cyst (by diagnosis and/or mammography), and without positive mammagraphy findings of malignancy or known allergic reaction to commercial lotions or creams.

Topical Administration: Oral instruction and written supervision was given. Each study participant was instructed to apply the emollient preparation of EXAMPLE 1 twice daily, i.e., morning and evening, in an amount equivalent to about ¼ to ½ teaspoon per breast including the area of the nipple.

Evaluation: Participants were instructed on techniques for personal breast examination to assess swelling, tenderness and pain, as well as, criteria to be used in completing a study questionaire on a once per week basis. According to those instructions, an arbitrary scale of 1 (none) to 5 (severe) was used to assess each of swelling and tenderness (i.e., pain). Under the conditions of the trial, participants were evaluated in office about once each 4 weeks, and a telephone conference was also employed (when necessary) to confirm and extend written records.

Clinical Indicia: Criteria for evaluating symptoms were: no change in severity values (I=0), decrease of one severity value (I=0.25), decrease of two severity values (I=0.50), three (I=0.75) and a decrease to a severity value of 0 or 1+(I=1.00).

Results: The results were compiled, and percentage change in values calculated for swelling, tenderness and pain at each of 4 weeks, 8 weeks, 12 weeks and 16 weeks of therapy. A summary of these results is presented in TABLE B, below.

personal physician, and 13 with cysts of unidentified origin, were followed and the number of cysts identified by palpation and/or mammography were recorded.

Clinical Indicia: The number of diagnosed cysts was recorded.

Observations: Under the conditions of this study, 61% of all study participants suffering from multiple cysts of unknown etiology showed at least a 75% reduction in the number of cysts; 23% of the participants showed a complete (100%) improvement (i.e., no palpable or mammographic evidence of a cyst after treatment; 76% of all participants with multiple cysts showed a 50% reduction in number of cysts. In participants suffering from fibroid cysts, 66% of participants with a single fibroid cyst showed complete (100%) improvement (i.e., no palpable cyst after treatment); and the remaining 34% of the participants showed a 75% reduction in the apparent size of the cyst (i.e., by palpation and/or mammography).

TABLE B

| | Percentage Amelioration of Severity (S)* | | | | | | | |
|---|---|---|---|---|---|---|---|---|
| | 4 WKS | | 8 WKS | | 12 WKS | | 16 WKS | |
| Clinical Indicia | No.[a] | %* | No.[a] | %* | No.[a] | %* | No.[a] | %* |
| Swelling | 8 | 63 ± −33 | 5 | 65 ± −29 | 4 | 69 ± −13 | 3 | 83 ± −14 |
| Tenderness/Pain | 16 | 70 ± −34 | 10 | 73 ± −30 | 7 | 82 ± −19 | 4 | 88 ± −14 |

*Amelioration (S) = mean improvement in severity value, "I" (supra) × 100%;
[a].) No. = number of evaluable patients at time point.

Observations: The following additional summary results were recorded in this study: namely, (i) 100% of the study participants who entered with menstration-associated breast tenderness showed 100% improvement; (ii) 80% of the study participants who entered the study with menstration-associated breast pain showed 100% improvement and the remaining 20% showed an improvement of at least 75%; (iii) 66% of the study participants who entered the study with menstration-associated breast swelling showed 100% improvement and the remaining 34% showed improvement of at least 75%; and (iv) 54% of study participants who entered the study with menstration-associated pain and fibroid cysts (or fibroid cyst pain only) showed 100% improvement, 42% showed 75% improvement and 8% showed at least 50% improvement.

EXAMPLE 3

Treatments of Fibroid Cysts in Adipose Tissues

Adipose tissues commonly constitute a loose connective tissue which is vascularized and contains fibroblasts, dendritic cells and variable numbers squamous epithelial cells. Exuberant synthesis of collagen, proteoglycans and other connective tissue proteins is believed responsible for formation of certain fibroid and lipid cysts, non-malignant fibromas and the like. A study was conducted to determine the effects of the emollient composition of EXAMPLE 1 (Preparation #3) on fibroid cysts.

Study Inclusion Criteria: Patients were asked to complete a short medical history. Inclusion criteria included diagnosis by palpation and/or mammography without positive mammography findings of malignancy.

Topical Administration: Instructions were given, as set forth in EXAMPLE 2, above.

Evaluation: Under the conditions of the trial, 13 participants with diagnosis of fibroid cysts, under the care of their

EXAMPLE 4

Treatments to Effect An Increase in the Volume of Adipose Tissues

During the course of the studies presented in EXAMPLES 2–4, above, some participants noted an increase in breast firmness, volume and bra size. A study was undertaken to determine the effects of the emollient composition of EXAMPLE 1 (Preparation #3) on breast enhancement.

Study Inclusion Criteria: Female volunteers were asked to complete a short medical history. Inclusion criteria included no evidence by palpation and/or mammography of malignancy, cysts, fibroid cysts, tenderness or pain.

Topical Administration: Instructions were given, as set forth in EXAMPLE 2, above.

Evaluation: Under the conditions of the trial, 22 participants were instructed according to EXAMPLE 2, and asked to score any observed changes in breast firmness, fullness and size on an arbitrary scale of 1 to 5.

Observations: Under the conditions of the study, 100% of the participants recorded an increase in fullness during the first 4 weeks of the study; 100% of the participants recorded an increase in firmness during the first 4 weeks of the study; 100% of the study participants recorded an increase in size during the first 4 weeks of the study; and no participant recorded any evidence of untoward reaction as a result of the treatment.

Citations

1. Dixon, J. M., McDonald, C., Elton, R. A. and W. R. Miller. 1999. Risk of breast cancer in women with palpable breast cysts: A prospective study. *Lancet* 353 (9166): 1742–1745.
2. Ader, D. N. and M. W. Browne. 1997. Prevalence and impact of cyclic mastalgia in a United States clinic-based sample. *Am J. Obstet. Gynecol.* 177 (1): 126–132.

3. Ayers, J. W. and G. P. Gidwani. 1983. The luteal breast: Hormonal and sonographic investigation of benign breast disease in patients with cyclic mastalgia. *Fertil. Steril.* 40: 779–784.
4. Hughes, L. E., Mansel, R. E. and D. J. T. Webster. 1987. Aberrations of normal development and involution (ANDI): A new perspective on pathogenesis and nomenclature of benign breast disorders. *Lancet* ii: 1316–1319.
5. Watts, J. F., Butt, W. R. and E. R. Logan. 1987. A clinical trial using danazol for the treatment of premenstrual tension. *Br. J. Obstet. Gynaecol.* 94: 30–34.
6. Gateley, C. A. and R. E. Mansel. 1990. Management of cyclical breast pain. *Br. J. Hosp. Med.* 43: 330–332.
7. Russell, L. C. 1989. Caffeine restriction as initial treatment for breast pain. *Nurse Pract.* 14: 36–37.
8. Rose, D. P., Boyar, A. P., Cohen, C. and L. E. Strong. 1987. Effect of low-fat diet on hormone levels in women with cystic breast disease. I. Serum steroids and gonadotropins. *J. Natl. Cancer Inst.* 78: 623–626.
9. Boyd, N. F., McGuire, V., Shannon, P., Cousins, M., Kriukov, V., Mahoney, L., et al. 1988. Effect of a low-fat high-carbohydrate diet on symptoms of cyclicl mastopathy. *Lancet* ii: 128–132.
10. Horrobin, D. F. and M. S. Manku. 1989. Premenstrual syndrome and premenstrual breast pain (cyclic myalgia): Disorders of essential fatty acid (EFA) metabolism. *Prostaglandins Leukot. Essent. Fatty Acids* 37: 255–261.
11. Haagensen, C. D., Bodian, C. and D. E. Haagensen. 1981. Breast carcinoma risk and detection. Philadelphia, W. B. Saunders.
12. Zhang, H. Y., Reddy, S. and T. A. Kotchen. 1999. A high sucrose, high linoleic acid diet potentiates hypertension in the Dahl salt sensitive rat. *Am. J. Hypertens.* 12 (2 Pt1): 183–187.
13. Yoshimoto-Furuie, K., Yoshimoto, K., Tanaka, T., Saima, S., Kikuchi, Y., Shay, J., Horrobin, D. F. and H. Echizen. 1999. Effects of oral supplementation with evening of primrose oil for six weeks on plasma essential fatty acids and uremic skin symptoms in hemodialysis patients. *Nephron* 81(2): 151–159.
14. Clandinin, M. T., Cheema, S., Field, C. J. and V. E. Baracos. 1993. Dietary lipids influence insulin action *Ann. N. Y. Acad. Sci* 683 (Jun. 14): 151–163.
15. Coyne, J. D., Parkinson, D. and A. D. Baildam. 1996. Membranous fat necrosis of the breast. *Histopathology* 28 (1): 61–64.
16. Marra, F., Riccardi, D., Melani, L., Spadoni, S., Galli, C., Fabrizio, P., Tosti-Guerra, C., Carloni, V., Gentilini, P. and G. Laffi. 1998. Effects of supplementation with unsaturated fatty acids on plasma and membrane lipid composition and platelet function in patients with cirrhosis and defective aggregation. *J. Hepatol.* 28 (4): 654–661.
17. Palombo, J. D., DeMichele, S. J., Lydon, E. E., Gregory, T. J., Banks, P. L., Forse, R. A. and B. R. Bistrian. 1996. Rapid modulation of lung and liver macrophage phospholipid fatty acids in endotoxemic rats by continuous enteral feeding with n-3 and gamma-linolenic fatty acids. *Am. J. Clin. Nutr.* 63 (2): 208–219.
18. O'Brien, S. N., Anandjiwala, J. and T. M. Price. 1997. Differences in estrogen content of breast adipose tissue in women by menopausal status and hormone use. *Obstet. Gynecol.* 90 (2): 244–248.
19. Rink, J. D., Simpson, E. R., Barnard, J. J. and S. E. Bulum. 1996. Cellular characterization of adipose tissue from various body sites of women. *J. Clin. Endocrinol. Metab.* 81 (7): 2443–2447.
20. Bulun, S. E., Sharda, G., Rink, J., Sharma, S. and E. R. Simpson. 1996. Distribution of aromatase P450 transcripts and adipose fibroblasts in the human breast. *J. Clin. Endocrinol. Metab.* 81(3): 1273–1277.
21. Price, T., Aitken, J., Head, J., Mahendroo, M., Means, G. and E. Simpson. 1992. Determination of aromatase P450 messenger ribonucleic acid in human breast tissue by competitive polymerase chain reaction amplification. *J. Clin. Endocrinol. Metab.* 74 (6): 1247–52.
22. Heber, D., Ashley, J. and D. Bagga. 1996. Stromal-epithelial cell interactions in breast cancer. *Adv. Exp. Med Biol.* 399: 41–51.
23. Ip, M. M., Masso-Welch, P. A., Shoemaker, S. F., Shea-Eaton, W. K. and C. Ip. 1999. Conjugated linoleic acid inhibits proliferation and induces apoptosis of normal rat mammary epithelial cells in primary culture. *Exp. Cell Res.* 250 (1): 22–34.
24. Brodie, A. E., Manning, V. A., Ferguson, K. R., Jewell, D. E. and C. Y. Hu. 1999. Conjugated linoleic acid inhibits differentiation of pre- and post-confluent 3T3-L1 preadipocytes but inhibits cell proliferation only in preconfluent cells. *J. Nutr.* 129 (3): 602–606.
25. Satory, D. L. and S. B. Smith. 1999. Conjugated linoleic acid inhibits proliferation but stimulates lipid filling of murine 3T3-L1 preadipocytes. *J. Nutr.* 129 (1): 92–97.
26. Bershtein, L. M., Barchuk, A. S., Lemekhov, V. G., Seleznev, I. K. and V. F. Semiglazov. 1983. [Morphometric and biochemical pecularities of fatty tissue in patients with cancer of the breast and lung.] (Russian) *Vopr. Onkol.* 29 (4): 45–51.
27. Wu, Z., Huber, J. T., Chan, S. C., Simas, J. M., Chen, K. H., Varela, J. G., Santos, F., Fontes, C. and P. Yu. 1994. Effect of source and amount of supplemental fat on lactation and digestion in cows. *J. Dairy Sci.* 77 (6): 1644–1651.
28. Munday, J. S., Thompson, K. G. and K. A. C. James. 1999. Dietary conjugated linoleic acid promotes fatty streak formation in the C57BL/6 mouse atherosclerosis model. *Br. J. Nutr.* 81: 251–255.
29. Sakono, M., Miyanaga, F., Kawahara, S., Yamauchi, K., Fukuda, N., Watanabe, K., Iwata, R. and M. Sugano. 1999. Dietary conjugated linoleic acid reciprocally modifies ketogenesis and lipid secretion by the rat liver. *Lipids* 34 (9): 997–1000.
30. Truitt, A., McNeill, G. and J. Y. Vanderhoek. 1999. Antiplatelet effects of conjugated linoleic acid isomers. *Biochim Biophys. Acta: Mol. Cell. Biol Lipids* 1438: 239–246.
31. Head, R. J., McLennan, P. L., Raederstorff, D., Muggli, R., Burnard, S. L. and E. J. McMurchie. 2000. Prevention of nerve conduction deficit in diabetic rats by polyunsaturated acids. *Am. J. Clin. Nutr.* 71 (1): 386S–392S.
32. Burnard, S. L., McMurchie, E. J., Leifert, W. R., Patten, G. S., Muggli, R., Raederstorff, D. and R. J. Head. 1998. Cilazapril and dietary gamma-linolenic acid prevent the deficit in sciatic nerve conduction velocity in the streptozotocin diabetic rat. *J. Diabetes Complications* 12 (2): 65–73.
33. Horrobin, D. F. 1997. Essential fatty acids in the management of impaired nerve function in diabetes. *Diabetes* 46 (Suppl. 2): S90–93.
34. Peterson, L. D., Thies, F. and P. C. Calder. 1999. Dose-dependent effects of dietary gamma-linolenic acid on rat spleen lymphocyte functions. *Prostaglandins Leukot. Essent. Fatty Acids* 61 (1): 19–24.
35. Ilc, K., Ferrero, J. M., Fischel, J. L., Formento, P., Bryce, R., Etiene, M. C. and G. Milano. 1999. Cytotoxic effects of two gamma linolenic salts (lithium gammalinolenate or meglumine gammalinolenate) alone or associated with a 35. nitrosourea: An experimental study on human glioblastoma cell lines. *Anticancer Drugs* 10 (4): 413–417.
36. Vartak, S., McCaw, R., Davis, C. S., Robbins, M. E. and A. A. Spector. 1998. Gamma-linolenic acid (GLA) is cytotoxic to 36B10 maliganant rat astrocytoma cells but not to 'normal' rat astrocytes. *Br. J. Cancer* 77(10): 1612–1620.
37. Jiang, W. G., Hiscox, S., Bryce, R. P., Horrobin, D. F. and R. E. Mansel. 1998. The effects of n-6 polyunsaturated fatty acids on the expression of nm-23 in human cancer cells. *Br. J. Cancer* 77 (5): 731–738.
38. Jiang, W. G., Hiscox, S., Horrobin, D. F., Bryce, R. P. and R. E. Mansel. 1997. Gamma linolenic acid regulates expression of maspin and the motility of cancer cells. *Biochem. Biophys. Res. Comm.* 237 (3): 639–644.
39. Jiang, W. G., Hiscox, S., Horrobin, D. F., Hallett, M. B., Mansel, R. E. and M. C. Puntis. 1995. Expression of catenins in human cancer cells and its regulation by n-6 polyunsaturated fatty acids. *Anticancer Res.* 15 (6B): 2569–2573.
40. Jiang, W. G., Bryce, R. P., Horrobin, D. F. and R. E. Mansel. 1998. Regulation of tight junction permeability and occludin expression by polyunsaturated fatty acids. *Biochem. Biophys. Res. Commun.* 244 (2): 414–420.
41. Munoz, S. E., Lopez, C. B., Valentich, M. A. and A. R. Eynard. 1998. Differential modulation by dietary n-6 or n-9 unsaturated fatty acids on the development of two murine mammary gland tumors having different metastatic capabilities. *Cancer Lett.* 126 (2): 149–155.
42. Ramchurren, N. and R. Karmali. 1995. Effects of gamma-linolenic acid and dihomo-gammalinolenic acids on 7,12-dimethylbenz(alpha)anthracene-induced mammary tumors in rats. *Prostaglandins Leukot. Essent. Fatty Acids.* 53 (2): 95–101.
43. Cesano, A., Visonneau, S., Scimeca, J. A., Kritchevsky, D. and D. Santoli. 1998. Opposite effects of linoleic acid and conjugated linoleic acid on human prostatic cancer in SCID mice. *Anticancer Research* 18 (3A): 1429–1434.
44. Visonneau, S., Cesano, A., Tepper, S. A., Scimeca, J. A., Santoli, D. and D. Kritchevsky. 1997. Conjugated linoleic acid suppresses the growth of human breast adenocarcinoma cells in SCID mice. *Anticancer Res.* 17 (2A): 969–973.
45. Wong, M. W., Chew, B. P., Wong, T. S., Hosick, H. L., Boylston, T. D. and T. D. Shultz. 1997. Effects of dietary conjugated linoleic acid on lymphocyte function and growth of mammary tumors in mice. *Anticancer Res.* 17 (2A): 987–993.
46. Cunningham, D. C., Harrison, L. Y. and T. D. Shultz. 1997. Proliferative response of normal human mammary and MCF-7 breast cancer cells to linoleic acid, conjugated linoleic acid and eicosanoid synthesis inhibitors in culture. *Anticancer Res.* 17 (1A): 197–203.
47. Rosenfeld, R. L., Kentsis, A., Deplewski, D. and N. Ciletti. 1999. Rat preputial sebocyte differentiation involves peroxisome proliferator-activator receptors. *J. Invest. Dermatol.* 112 (2): 226–232.
48. Frohnert, B. I., Hui, T. Y. and D. A. Bernlohr. 1999. Identification of a functional peroxisome proliferator-responsive element in the murine fatty acid transport protein gene. *J. Biol. Chem.* 274 (7): 3970–3977.
49. Mueller, E., Sarraf, P., Tontonoz, P., Evans, R. M., Martin, K. J., Zhang, M., Fletcher, C., Singer, S. and B. M. Spiegelman. 1998. Terminal differentiation of human breast cancer through PPAR gamma. *Mol. Cell.* 1 (3): 465–470.
50. Sarraf, P., Mueller, E., Smith, W. M., Wright, H. M., Kum, J. B., Aaltonen, L. A., de la Chapelle, A., Spiegelman, B. M. and C. Eng. 1999. Loss-of-function mutations in PPAR gamma associated with human colon cancer. *Mol. Cell.* 3 (6): 799–804.
51. Chamras, H., Bagga, D., Elstner, E., Setoodeh, K., Koeffler, H. P. and D. Heber. 1998. Preadipocytes stimulate breast cancer cell growth. *Nutr. Cancer* 32 (2): 59–63.
52. Jahreis, G., Fritsche, J., Mockel, P., Schone, F., Moller, U. and H. Steinhart. 1999. The potential anticarcinogenic conjugated linoleic acid, cis-9, trans-11 C18:2, in milk of different species: Cow, goat, ewe, sow, mare, woman. *Nutr. Res.* 19 (10): 1541–1549.
53. Ma, D. W. L., Wierzbicki, A. A., Field, C. J. and M. T. Clandinin. 1999. Conjugated linoleic acid in Canadian dairy and beef products. *J. Agric. Food Chem.* 47: 1956–1960.
54. Adlof, R. O. 1999. The Lindlar-catalyzed reduction of methyl santalbate: A facile preparation of methyl 9-cis, 11-trans-octadecadienoate-9,10-d(2). *J. Am. Oil Chem. Soc.* 76: 301–304.
55. Chen, C. A. and C. J. Sih. 1999. Synthesis of 9Z, 11E-octadecadienoic and 10E, 12Z-octadecadienoic acids, the major components of conjugated linoleic acid. *Lipids* 34 (8): 879–884.
56. Eulitz, K., Yurawecz, M. P., Sehat, N., Firtsche, J., Roach, J. A. G., Mossoba, M. M., Kramer, J. K. G., Adlof, R. O. and Y. Ku. 1999. Preparation, separation and confirmation of the eight geometrical cis/trans conjugated linoleic acid isomers 8,10-through 11,13-18:2. *Lipids* 34 (8): 873–877.
57. Kurenzi, F. M. and N. Dale. 1996. Effect of capsaicin and analogues on potassium and calcium currents and vanilloid receptors in Xenopus embryo spinal neurones. *Br. J. Pharmacol.* 119 (1): 81–90.
58. Routledge, E. J., Parker, J., Odum, J., Ashby, J. and J. P. Sumpter. 1998. Some alkyl hydroxy benzoate preservatives (parabens) are estrogenic. *Toxicol. Appl. Pharmacol.* 153(1): 12–19.)
59. Raychowdhury, M. K., Goswami, R., and P. Chakrabarti. 1985. Effect of unsaturated fatty acids in growth inhibition of some penicillin-resistant and sensitive bacteria. *J. Appl. Bacteriol.* 59 (2): 183–188.
60. Altenbern, R. A. 1977. Effects of exogenous fatty acids on growth and enterotoxin B formation by *Staphylcoccus aureus* 14458 and its membrane mutant. *Can. J. Microbiol.* 23 (4): 389–397.
61. Kaparal, F. A., Smith, S., and D. Lal. 1992. The esterification of fatty acids by *Staphylococcus aureus* fatty acid modifying enzyme (FAME) and its inhibition by glycerides. *J. Med. Microbiol.* 37 (4): 235–237.)
62. Butcher, G. W., King, F. and K. G. Dyke. 1976. Sensitivity of *Staphylcoccus aureus* to unsaturated fatty acids. *J. Gen. Microbiol.* 94 (2): 290–296.
63. Jacques, N. A., Jacques, V. L., Wolf, A. C. and C. L. Wittenberger. 1985. Does an increase in membrane unsaturated fatty acids account for Tween 80 stimulation of glucosyltransferase secretion by Streptococcus salivarius? *J. Gen. Microbiol.* 131 (1): 67–72.
64. The Merck Index, Tenth Edition, Entry 7048, p. 1033 (1983)
65. International Cosmetic Ingredient Dictionary, Fifth Edition, vol. 1, p.415–417 (1993)
66. International Cosmetic Ingredient Dictionary, Fifth Edition, vol. 1, p.537 (1993)
67. Schindler, et. al. Drug. Cosmet. Ind., 89, 36–37, 76, 78–80, 82 (1961)

While the preferred embodiment of the invention has been illustrated and described, it will be appreciated that various changes can be made therein without departing from the spirit and scope of the invention.

I claim:

1. An emollient composition for topical administration of a safe and effective dosage of a $C_{18}$ unsaturated fatty acid to a subject in need thereof, comprising a carrier, a vehicle, a penetrant, a mixture of $C_{16}$ and $C_{20}$ fatty acids in a hydrophobic phase with said $C_{18}$ unsaturated fatty acid, a natural anti-inflammatory compound, a natural estrogenic compound and a fragrance, wherein:

said $C_{18}$ unsaturated fatty acid is selected from the group consisting of a $C_{18:1}$ fatty acid, a $C_{18:2}$ fatty acid, a $C_{18:3}$ fatty acid and unsaturated derivatives and mixtures thereof;

said emollient composition comprises greater than about 3% by weight of said $C_{18}$ unsaturated fatty acid;

said vehicle comprises water, ethanol, propylene glycol and glycerin;

said penetrant is selected from the group consisting of urea, imidurea, palmitate, isopropyl palmitate, isoproyl myristate, propylene glycol and nonionic detergents;

said $C_{16}$ and $C_{20}$ fatty acids are selected from the group consisting of $C_{16:0}$, $C_{16:1}$, $C_{20:3}$, $C_{20:4}$ and derivatives and mixtures thereof;

said natural anti-inflammatory compound is selected from the group consisting essentially of herbal anti-inflammatory compounds include unpurified and substantially purified oils collected from a Chamomilla species, a Matricaria species, an Artemisia species, an Achillea species and species genetically related thereto; and, said natural estrogenic agent comprises an alkyl-hydroxybenzoate compound capable of stimulating estrogen synthesis in an adipose tissue.

2. The emollient composition of claim 1, wherein said $C_{18}$ unsaturated fatty acid further comprises a fatty acid selected from the group consisting of a linoleic acid, a conjugated linoleic acid, a linolenic acid, an alpha-linolenic acid, a gamma-linolenic acid and derivatives and mixtures thereof.

3. The emollient composition of claim 1, wherein said carrier comprises a 2-propenoic acid polyacrylic homopolymeric carrier.

4. The emollient composition of claim 1, wherein said 2-propenoic acid polyacrylic homopolymeric carrier is selected from the group consisting of Carbomer 940, Carbomer 934P, Carbomer 934, Carbomer 1342 and polyacrylic acid polymeric derivatives and mixtures thereof.

5. The emollient composition of claim 1, wherein said nonionic detergent is selected from the group consisting of oleyl esters, stearyl ethers, polyoxyethylene glycol esters of $C_{18}$ saturated fatty acids, PEG fatty acid esters, ethoxylated fatty acid esters, and macrogol fatty acid esters.

6. The emollient composition of claim 5, wherein said oleyl esters are selected from the group consisting of Brij 98, Brij 99 and mixtures and derivatives thereof.

7. The emollient composition of claim 6 wherein said stearyl ethers are selected from the group consisting essentially of Brij 721 ($C_{18}$ $E_{21}$), Brij 78 ($C_{18}E_{20}$), Brij 76 ($C_{18}E_{10}$), Brij 96 ($C_{18-1E10}$) and Brij 721 ($C_{18}E_{21}$) and mixtures and derivatives thereof.

8. The emollient composition of claim 7, further comprising about 1.0% (w/w) to about 6.0% (w/w) urea; 0.5% (w/w) to about 1.5% (w/w) Brij 99; about 1% to about 15% isopropyl palmitic acid; and about 2% to about 10% propylene glycol.

9. The emollient composition of claim 8, further comprising about 1% to about 3% (w/w) urea; about 0.5% to about 1.5% (w/w) Brij 99; about 1% to about 8% isopropyl palmitic acid; about 2% to about 6% propylene glycol.

10. The emollient composition of claim 1, wherein said $C_{16}$ and $C_{20}$ fatty acids are selected from the group consisting of palmitic acid, palmitoleic acid, di-hydro-gamma-linolenic acid, arachidonic acid and derivatives and mixtures thereof.

11. The emollient composition of claim 1, wherein all of said $C_{18}$ unsaturated fatty acids and said $C_{16}$, $C_{20}$ fatty acids comprise a natural stable oil cold extracted from a vegetable, a seed, a nut or a bean.

12. The emollient composition of claim 4, wherein said natural stable oil comprises vegetable, seed, bean oil about 1.6 times to about 2-times more polyunsaturated fatty acids than saturated fatty acids and contains less than about 3% by weight of cholesterol, triglycerides or phospholipids.

13. The emollient composition of claim 12, wherein said natural stable oil further comprises greater than about 40% of the total fatty acids present as said $C_{18}$ unsaturated fatty acids.

14. The emollient composition of claim 13, wherein said natural stable oil comprises greater than about 40% of the total fatty acids present as $C_{18:2}$ and $C_{18:3}$ fatty acids.

15. The emollient composition of claim 14, wherein said natural stable oil comprises greater than about 40% of the total fatty acid present as fatty acids selected from the group consisting of linoleic acid, conjugated linoleic acid, alpha-linolenic acid, gamma-linolenic acid and derivatives and mixtures thereof.

16. The emollient composition of claim 15, wherein said natural stable oil is selected from the group consisting of a hemp oil, a chia oil, a kukui oil, a flax oil, a soybean oil, a cottonseed oil, a walnut oil, a wheat germ oil, an evening primrose oil, a safflower oil, a grape oil, a canola oil, a sunflower seed oil, a blackcurrant oil, a borage oil, a corn oil, a sesame oil and mixtures thereof.

17. The emollient composition of claim 16, wherein said stable oil is further selected from the group consisting of a cottonseed oil, a hemp oil, a chia oil, a kukui oil, a flax oil, a soybean oil, a walnut oil, a wheat germ oil, an evening primrose oil, a borage oil and mixtures thereof.

18. The emollient composition of claim 1, wherein said natural anti-inflammatory compound is selected from the group consisting essentially of herbal anti-inflammatory compounds include unpurified and substantially purified oils collected from a Chamomilla species, a Matricaria species, an Artemisia species, an Achillea species and species genetically related thereto.

19. The emollient composition of claim 18, wherein said natural anti-inflammatory compound comprises a compound selected from the group consisting of a bisabolol, a levomenol, a tiglic acid ester, an azulene and derivatives and mixtures thereof.

20. The emollient composition of claim 19, wherein said bisabolol compound is selected from the group consisting of alpha-bisabolol, a hydroxy-bisabolol, 6-methyl-2-(4-methyl-3 cyclohexen-1-yl)-5-hepten-2-ol (alpha bisbolol) and derivatives and mixtures thereof.

21. The emollient composition of claim 19, wherein said tiglic acid ester comprises an (E)-2-methyl-2-butenoic acid or derivatives thereof.

22. The emollient composition of claim 19, wherein said azulene comprises a 7-ethyl-1,4-dimethylazulene or a derivative thereof.

23. The emollient composition of claim 1, wherein said natural estrogenic agent comprises an alkyl-hydroxybenzoate compound capable of stimulating estrogen synthesis in an adipose tissue.

24. The emollient composition of claim 23, wherein said compound comprises a compound selected from the group consisting of a paraben, a methylparaben, a propylparaben, a butyl-paraben and derivatives and mixtures thereof.

25. A method for topically administering a safe and effective dosage of a $C_{18}$ fatty acid to a subject in need thereof comprising the step of administering the composition of claim 1, wherein said dosage and said topical administration are effective to induce a metabolic change in a subcutaneous adipose tissue.

26. The method of claim 25, wherein said subject in need thereof of comprises a human or a domestic animal.

27. The method of claim 26, wherein said human subject in need exhibits one or more indicia of disease, wherein said indicia is selected from the group consisting of a premenstral pain, a mammary inflammation, a fibroid cyst, a lipid cyst, a post-menopausal estrogen insufficiency; a cyclic mastalgia, a benign breast pain, a premenstral breast pain or tenderness, a mammary swelling, a fibrocystic disease, a mammary nodule, a mammary cysts, a fibroadenoma, a mammary carcinoma, a vascular or neuropathic complication of long-term diabetes, an impairment of fertility, a low breast milk production, a high blood pressure in an adipose tissue, a restriction of blood flow in the microvasculature of an adipose tissue, a menopausal hot flash, a skin or mucous membrane complication of Sjogren's autoimmune syndrome and a skin or peripheral neuropathic complications of shingles.

28. The method of claim 26, wherein said human subject in need exhibits one or more indicia of cosmetic need, wherein said indicia is selected from an undesirable feature of a cutaneous keratinized epithelium or of a cornified epithelium, an undesirable feature of a mammary gland and an undesirable feature of a tissue containing adipose cells.

29. The method of claim 28, wherein said undesirable feature of a cutaneous keratinized epithelium is selected from the group consisting of a psoriasis, a dermatitis, an atopic dermatitis, a scaly itchy skin, a eczema, a scar, a wrinkle, a skin line and an age related dryness of skin.

30. The method of claim 28, wherein said undesirable feature of a cornified epithelium is selected from the group consisting of a splitting finger or toe nail, a discolored finger nail or toe nail, an irregularly shaped grooved or ridged fingernail or toe nail and a corneal ophthalmic tissue.

31. The method of claim 28, wherein said undesirable feature of a tissue containing an adipose cells is selected from the group consisting of a loss of cutaneous tissue tension, a tissue sagging, a decrease in tissue volume, a lack of tissue firmness and a lack of tissue fullnesss.

32. The method of claim 31, wherein said undesirable feature comprises a complication of age, cancer cachesia, cancer chemotherapy, starvation, malnutrition or dieting.

33. A method for increasing the tissue volume, firmness, and fullness of a subcutaneous adipose tissue, comprising the step of topically administering the composition of claim 1 to a subject having one or more indicia of cosmetic need.

34. A method for treating a subject in need thereof to ameliorate a symptom of a disease or a cosmetic indicia of need, comprising the step of administering to said subject an emollient cream comprising a $C_{18}$ fatty acid, wherein said $C_{18}$ fatty acid is selected from among a $C_{18:1}$ fatty acid, a $C_{18:2}$ fatty acid, a $C_{18:3}$ fatty acid and derivatives and mixtures thereof;

wherein said symptom of disease comprises a premenstral pain, a mammary inflammation, a fibroid cyst, a lipid cyst, a post-menopausal estrogen insufficiency; a cyclic mastalgia, a benign breast pain, a premenstrul breast pain or tenderness, a mammary swelling, a fibrocystic disease, a mammary nodule, a mammary cyst, a fibroadenoma, a mammary carcinoma, a vascular or neuropathic complication of long-term diabetes, an impairment of fertility, a low breast milk production, a high blood pressure in an adipose tissue, a restriction of blood flow in the microvasculature of an adipose tissue, a menopausal hot flash, a skin or mucous membrane complication of Sjogren's autoimmune syndrome and a skin or peripheral neuropathic complications of shingles; and, wherein said cosmetic indicia of need comprises a cutaneous keratinized epithelium or of a cornified epithelium, an undesirable feature of a mammary gland and an undesirable feature of a tissue containing adipose cells.

35. A method for delayed and sustained topical administration of an essential unsaturated $C_{18}$ fatty acid to a subject in need thereof, comprising the step of administering to the resident skin bacterial flora of said subject all of the following: namely, a balanced metabolic mixture of fatty acids; an agent effect to stimulate bacterial fatty acid synthesis; an agent effective to inhibit bacterial growth and promote release of said $C_{18}$ unsaturated fatty acid at said topical site; wherein said balanced mixture of fatty acids comprises a mixture of saturated $C_{16}$ fatty acids, saturated $C_{18}$ fatty acids and unsaturated $C_{20-22}$ fatty acids.

\* \* \* \* \*